(12) United States Patent
Mounier et al.

(10) Patent No.: US 10,233,500 B2
(45) Date of Patent: Mar. 19, 2019

(54) MICRORNAS CHARACTERIZING ROSACEA AND THE USES THEREOF

(71) Applicant: GALDERMA RESEARCH & DEVELOPMENT, Biot (FR)

(72) Inventors: Carine Mounier, Valbonne (FR); Sophie Deret, Mougins (FR)

(73) Assignee: GALDERMA RESEARCH & DEVELOPMENT, Biot (FR)

(*) Notice: Subject to any disclaimer, the term of this patent is extended or adjusted under 35 U.S.C. 154(b) by 0 days.

(21) Appl. No.: 15/502,395

(22) PCT Filed: Aug. 6, 2015

(86) PCT No.: PCT/FR2015/052171
§ 371 (c)(1),
(2) Date: Feb. 7, 2017

(87) PCT Pub. No.: WO2016/020625
PCT Pub. Date: Feb. 11, 2016

(65) Prior Publication Data
US 2017/0233814 A1    Aug. 17, 2017

(30) Foreign Application Priority Data
Aug. 7, 2014   (FR) ..................................... 14 57668

(51) Int. Cl.
*C07H 21/02*    (2006.01)
*C07H 21/04*    (2006.01)
*C12Q 1/6883*   (2018.01)
*G01N 33/50*    (2006.01)

(52) U.S. Cl.
CPC ....... *C12Q 1/6883* (2013.01); *G01N 33/5023* (2013.01); *C12Q 2600/106* (2013.01); *C12Q 2600/136* (2013.01); *C12Q 2600/158* (2013.01); *C12Q 2600/178* (2013.01)

(58) Field of Classification Search
CPC .......................... C12N 15/113; C12N 2310/11
See application file for complete search history.

(56) References Cited

FOREIGN PATENT DOCUMENTS

WO      2005118806 A2    12/2005
WO      2011053257 A2    5/2011
WO      WO 2011/057003 A2 *  5/2011  ......... C12N 2310/11

OTHER PUBLICATIONS

International Search Report dated Nov. 4, 2015 corresponding to International Patent Application No. PCT/FR2015/052171, 6 pages.
Genechip: "Data Sheet GeneChip TM miRNA 3.0 Array," Mar. 2012, XP055222758 [retrieved from the Internet on Oct. 21, 2015], 4 pages.

* cited by examiner

*Primary Examiner* — Amy H Bowman
(74) *Attorney, Agent, or Firm* — Sunit Talapatra; Foley & Lardner LLP

(57) ABSTRACT

The invention relates to the identification of mircoRNAs associated with rosacea and to the uses thereof. More specifically, the invention relates to a method of diagnosing rosacea in a subject, comprising the determination, in a sample from said subject, of the expression of at least the combination of the following seven microRNAs: hsa-miR-3201, hsa-miR-4423-3p, hsa-miR-3128, hsa-miR-3163, hsa-miR-606, hsa-miR-4776-5p and hsa-miR-635.

7 Claims, No Drawings

MICRORNAS CHARACTERIZING ROSACEA AND THE USES THEREOF

CROSS-REFERENCE TO PRIOR APPLICATIONS

This application is a National Stage of PCT/FR2015/052171, filed Aug. 6, 2015, and designating the United States (published on Feb. 11, 2016, as WO 2016/020625 A1), which claims priority under 35 U.S.C. § 119 to French Application No. 1457668, filed Aug. 7, 2014, each hereby expressly incorporated by reference in its entirety and each assigned to the assignee hereof.

The present invention relates to the field of medicine and more particularly to the diagnosis and the treatment of rosacea.

PRIOR ART

The name "rosacea" refers to the characteristic color appearing on the patient's face. Although it does not have serious consequences for the individual's health, rosacea may have significant psycho-affective consequences.

Rosacea seldom begins before the age of 30, and its frequency gradually increases up to a peak around 40/50 years of age. One study has shown a greater frequency of subtype I (about 45% of rosacea patients) compared with subtype II (about 25%). Furthermore, type I rosacea mostly affects women (about two-thirds of patients) whereas type II forms of rosacea have not shown differences in distribution by sex.

Rosacea is wrongly associated with overconsumption of alcohol or with acne. Despite its frequency, its causes remain poorly established. Diet and climatic factors play a part in the disease and have an impact on its symptoms. Although rosacea has been known for some time and affects many patients, its causes have not been elucidated to date. A genetic predisposition is suspected: 40% of individuals affected by a form of rosacea have a member of their family also affected.

Many factors are regarded as promoting/triggering the appearance of rosacea, such as: emotional stress, hot beverages, alcohol, spicy food, physical exercise, extreme temperatures and sudden temperature changes, hot baths/showers, etc.

All these factors tend to promote vasomotor flushes, promoting the triggering of the pathology. Rosacea is characterized by:
- Vascular and vasomotor problems, especially with vasodilatation of the vessels promoting the appearance of telangiectasias.
- Inflammation expressed as an immune response with recruitment of innate immune cells (macrophages, neutrophils, dendritic cells) and acquired immune cells (Th1 lymphocytes, antibody-secreting B-lymphocytes, cytotoxic T-cells). At the molecular level, this inflammation is exacerbated in subtype II. The loose connective tissue of the skin relaxes (actinic elastosis), which is also found in photoaging phenomena and which may also be due to the patient's age.

Erythematotelangiectatic rosacea (ETR), or type I rosacea (RI), is the most common form characterized by persistent redness, or erythema. It is generally concentrated in the center of the face, while sparing the perimeter of the eyes and that of the mouth, but while including the cheeks, the nose, the middle of the forehead and the chin. In this form, redness is accompanied by heightened skin sensitivity which makes it difficult to apply cosmetics. Skin coloring may be associated with the development of small, very fine, very red and occasionally even purplish vessels visible beneath the skin surface: telangiectasias. This form is also often accompanied by classic symptoms of hot flashes.

In papulopustular rosacea (PPR), or type II rosacea (RII), papules and/or pustules resembling acne lesions may appear on the erythema, whence the name papulopustular rosacea. Papules are red, firm and sometimes painful raised areas of skin measuring one to four millimeters and which are surrounded by an inflammatory ring. They sometimes reflect invasion of the sebaceous gland by a parasite called *Demodex folliculorum*, usually present in the follicle. Pustules are often smaller than papules and may develop outside any infectious context.

Thus, it remains difficult to distinguish acne vulgaris-type acne from rosacea, particularly type II rosacea.

SUMMARY OF THE INVENTION

The present invention provides a method for diagnosing rosacea, particularly type II, in a subject, comprising determining in a sample from said subject the expression of at least the combination of the following seven microRNAs: hsa-miR-3201, hsa-miR-4423-3p, hsa-miR-3128, hsa-miR-3163, hsa-miR-606, hsa-miR-4776-5p and hsa-miR-635.

These microRNAs are thus useful as biomarkers of rosacea. More precisely, they are specific biomarkers of type II rosacea, the expression of which is altered neither in normal subjects nor in subjects having type I rosacea. Likewise, the expression of these microRNAs is not altered in patients suffering from acne, although these two pathologies are difficult to distinguish.

The invention also relates to a kit comprising means for specifically detecting these following seven microRNAs, and to the use of same for diagnosing rosacea, for screening molecules likely to be used to treat rosacea, for distinguishing type II rosacea from type I rosacea, or for determining the efficacy of a treatment for rosacea, preferably type II rosacea.

DESCRIPTION OF THE INVENTION

Definitions

MicroRNAs

MicroRNAs are small non-coding RNAs of 18 to 25 nucleotides, expressed in most eukaryotic organisms, which play an important role in the regulation of gene expression. They are powerful post-transcriptional repressors: by binding by complementarity to specific nucleotide sequences present on mRNAs, they prevent these so-called "target" transcripts from being translated into proteins. A microRNA has several target mRNAs and, conversely, an mRNA is the target of several microRNAs.

All known microRNAs are listed in the miRBase database (miRBase, http://www.mirbase.org). Homologous microRNAs can be found in several organisms; an annotation system has thus been set up to assign a single identifier thereto. MicroRNAs are identified by a number preceded by the abbreviation "miR" or "mir", which allows a distinction between the mature microRNA (miR) and the stem-loop structure of the microRNA precursor (mir). A prefix is used to distinguish between species, such as, for example, hsa-miR-101 and mmu-miR-101 to distinguish between the human microRNA (hsa: *Homo sapiens*) and the mouse microRNA (mmu: *Mus musculus*). In certain cases, the same stem-loop precursor can give rise to the synthesis of two different microRNAs. The annotation system allows a distinction between these two microRNAs: the microRNA from the 5' side of the loop is denoted 5p and the microRNA from the 3' side is denoted 3p. This 3p and 5p annotation is used until the abundance of one of the two forms is determined. The majority form "miR-xxx" is then distinguished from the minority form "miR-xxx*".

MicroRNAs are involved in a wide range of key biological processes, such as cell cycle control and apoptosis. They also regulate several physiological and developmental processes, such as stem cell differentiation, hematopoiesis, hypoxia, muscle development, neurogenesis, insulin secretion, cholesterol metabolism, aging and immune and inflammatory responses. Moreover, distinct patterns of temporal expression during embryogenesis and tissue-specific expression profiles suggest that microRNAs play an essential role in tissue differentiation and maintenance of identity. These biological processes are often dysregulated in affected individuals. Numerous studies have shown the involvement of microRNAs in certain pathologies, including various cancers, cardiac diseases and neurological disorders. More recently, the role of microRNAs was also shown in certain dermatological diseases such as psoriasis, vitiligo and certain skin cancers.

Subjects

The subjects are human patients, men or women, of any age, preferably over 18.

Biological Samples

The samples tested are typically samples of dermis, of epidermis or of dermis and epidermis. In certain embodiments, it is a skin biopsy, preferably taken from affected regions of the skin. It may also be any sample of biological fluid, such as blood, saliva or urine.

Controls

The control samples, or the control expression levels, are samples, or expression levels, from healthy subjects or subjects having another pathology, potentially another skin pathology.

Diagnostic Applications

The present invention relates to the identification of microRNAs and/or precursors thereof which are differentially expressed in subjects suffering from rosacea compared with healthy subjects or subjects having another skin pathology, such as acne. In particular, it relates to the identification of microRNAs and/or precursors thereof which are differentially expressed in subjects suffering from type II rosacea compared with healthy subjects and/or subjects suffering from type I rosacea. Based on the identified microRNAs, it is possible to:
- use these microRNAs as biomarkers of rosacea or a subtype of rosacea, in particular subtype II;
- use one or more identified microRNAs for the diagnosis, detection, subtype determination, monitoring and prognosis of rosacea;
- carry out a method of diagnosis, detection, subtype determination, monitoring and prognosis of rosacea, the method comprising at least one step of determining the level of expression of one or more identified microRNAs in a patient sample;
- prepare a kit for the diagnosis, detection, subtype determination, monitoring and prognosis of rosacea, the kit comprising means for detecting the expression level of one or more identified microRNAs. Preferably, the detection means are nucleic acids or peptides having a capacity to bind to one or more identified microRNAs, preferably specific oligonucleotides or probes of one or more identified microRNAs;
- carry out a method for monitoring the therapeutic efficacy of a treatment wherein a step of determining the expression level of one or more identified microRNAs in a patient sample is carried out before, during and/or after treatment and the expression levels are compared;
- use these microRNAs to perform population or cluster analyses, for example to differentiate subjects suffering from type I rosacea and those suffering from subtype II rosacea, subjects suffering from rosacea and healthy subjects, or subjects suffering from type II rosacea and healthy subjects.
- use these microRNAs to perform population or cluster analyses, for example to differentiate subjects suffering from rosacea and subjects suffering from acne.

Once the diagnosis is made, a rosacea treatment can be envisaged. When type II rosacea has been diagnosed, a treatment with for example doxycycline (orally), or with topical metronidazole or ivermectin, may be prescribed.

An object of the invention thus relates to a method for diagnosing rosacea in a subject, comprising determining in a sample from said subject the expression of at least the combination of the following seven microRNAs: hsa-miR-3201, hsa-miR-4423-3p, hsa-miR-3128, hsa-miR-3163, hsa-miR-606, hsa-miR-4776-5p and hsa-miR-635. The patient is deemed to suffer from rosacea if the expression of these microRNAs is greater than that of the control subjects.

Advantageously, the method may comprise additionally determining the expression of one or more microRNAs selected from

| | |
|---|---|
| hsa-miR-133a | hsa-miR-3201 |
| hsa-miR-133b | hsa-miR-4423-3p |
| hsa-miR-1 | hsa-miR-3128 |
| hsa-miR-299-5p | hsa-miR-155 |
| hsa-miR-486-3p | hsa-miR-3163 |
| hsa-miR-381 | hsa-miR-146b-5p |
| hsa-miR-4324 | hsa-miR-606 |
| hsa-miR-154 | hsa-miR-150 |
| hsa-miR-1247 | hsa-miR-4776-5p |
| hsa-miR-1287 | hsa-miR-3124-5p |
| hsa-miR-376c | hsa-miR-4741 |
| hsa-miR-195* | hsa-miR-635 |
| hsa-miR-4269 | hsa-miR-4668-5p |
| hsa-miR-1296 | hsa-miR-4763-3p |
| hsa-miR-34c-3p | hsa-miR-4417 |
| hsa-miR-204 | hsa-miR-1911* |
| hsa-miR-504 | hsa-miR-4734 |
| hsa-miR-30c-1* | hsa-miR-4530 |
| hsa-miR-615-3p | hsa-miR-4260 |
| hsa-miR-505 | hsa-miR-3185 |
| hsa-miR-508-5p | hsa-miR-4707-5p |
| hsa-miR-409-5p | hsa-miR-4745-5p |
| hsa-miR-433 | hsa-miR-4659a-3p |
| hsa-miR-375 | hsa-miR-1469 |
| hsa-miR-935 | hsa-miR-4695-5p |
| hsa-miR-128 | hsa-miR-4674 |
| hsa-miR-331-5p | hsa-miR-4687-3p |
| hsa-miR-584 | hsa-miR-4739 |
| hsa-miR-30a* | hsa-miR-1915 |
| hsa-miR-370 | hsa-miR-216b |
| hsa-miR-148a* | hsa-miR-548a-3p |
| hsa-miR-489 | |
| hsa-miR-30e* | |
| hsa-miR-337-5p | |
| hsa-miR-1181 | |
| hsa-miR-1237 | |
| hsa-miR-485-5p | |
| hsa-miR-23c | |
| hsa-miR-148b | |
| hsa-miR-378g | |
| hsa-miR-1238 | |

-continued hsa-miR-181a-2*
hsa-miR-187
hsa-miR-378d
hsa-miR-181d
hsa-miR-98
hsa-miR-4685-3p
hsa-miR-23b*

An altered expression level of at least one of these microRNAs relative to the expression level in control subjects reinforces the diagnosis.

According to a particular aspect, the expression of one or more microRNAs is furthermore determined, said RNAs being selected from one of the groups consisting of 1) hsa-miR-133a, hsa-miR-206, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-411, hsa-miR-4269, hsa-miR-328, hsa-miR-1296, hsa-miR-34c-3p, hsa-miR-204, hsa-miR-504, hsa-miR-30c-1*, hsa-miR-615-3p, hsa-miR-654-3p, hsa-miR-505, hsa-miR-508-5p, hsa-miR-409-5p, hsa-miR-338-5p, hsa-miR-433, hsa-miR-375, hsa-miR-935, hsa-let-7d*, hsa-miR-99a*, hsa-miR-128, hsa-miR-1290, hsa-miR-331-5p, hsa-miR-4730, hsa-miR-29c*, hsa-miR-455-5p, hsa-miR-377*, hsa-miR-378e, hsa-miR-584, hsa-miR-96, hsa-miR-30a*, hsa-miR-143*, hsa-miR-370, hsa-miR-148a*, hsa-miR-489, hsa-miR-506, hsa-let-7e*, hsa-miR-30e*, hsa-miR-4787-3p, hsa-let-7b*, hsa-miR-181c*, hsa-miR-513a-5p, hsa-miR-92a-1*, hsa-miR-337-5p, hsa-miR-1181, hsa-miR-1237, hsa-miR-3620, hsa-miR-485-5p, hsa-miR-23c, hsa-miR-18a*, hsa-miR-10a, hsa-miR-139-3p, hsa-miR-493, hsa-miR-148b, hsa-miR-550a, hsa-miR-3147, hsa-miR-378g, hsa-miR-675*, hsa-miR-1238, hsa-miR-542-5p, hsa-miR-30c-2*, hsa-miR-125a-3p, hsa-miR-181a-2*, hsa-miR-1292, hsa-miR-187, hsa-miR-378*, hsa-miR-493*, hsa-miR-495, hsa-miR-557, hsa-miR-3909, hsa-miR-378d, hsa-miR-491-5p, hsa-miR-181d, hsa-miR-671-3p, hsa-miR-513c, hsa-miR-487b, hsa-miR-378b, hsa-miR-885-5p, hsa-miR-98, hsa-miR-29b-2*, hsa-miR-4685-3p, hsa-miR-3605-3p, hsa-miR-24-1*, hsa-miR-4649-3p, hsa-miR-3180-5p, hsa-miR-149, hsa-miR-23b*, hsa-miR-4758-5p, hsa-miR-4665-5p, hsa-miR-149*, hsa-miR-548ac, hsa-miR-4507, hsa-miR-548a-3p, hsa-miR-4289, hsa-miR-4727-3p, hsa-miR-4468, hsa-miR-4463, hsa-miR-2861, hsa-miR-4773, hsa-miR-1825, hsa-miR-4651, hsa-miR-216b, hsa-miR-4689, hsa-miR-3152-3p, hsa-miR-4270, hsa-miR-1915, hsa-miR-4739, hsa-miR-4772-5p, hsa-miR-4687-3p, hsa-miR-4674, hsa-miR-4695-5p, hsa-miR-4439, hsa-miR-129-3p, hsa-miR-1469, hsa-miR-4659a-3p, hsa-miR-4799-3p, hsa-miR-4657, hsa-miR-4655-5p, hsa-miR-4745-5p, hsa-miR-4662b, hsa-miR-4707-5p, hsa-miR-3185, hsa-miR-4260, hsa-miR-4530, hsa-miR-4734, hsa-miR-1911*, hsa-miR-4417, hsa-miR-4763-3p, hsa-miR-4668-5p, hsa-miR-1281, hsa-miR-635, hsa-miR-4741, hsa-miR-3124-5p, hsa-miR-146b-3p, hsa-miR-4529-3p, hsa-miR-4776-5p, hsa-miR-150, hsa-miR-3927, hsa-miR-606, hsa-miR-146b-5p, hsa-miR-3163, hsa-miR-155, hsa-miR-371b-5p, hsa-miR-3128, hsa-miR-4423-3p, hsa-miR-335, hsa-miR-3201, hsa-miR-184

2) hsa-miR-206, hsa-miR-133b, hsa-miR-133a, hsa-miR-1, hsa-miR-486-3p, hsa-miR-299-5p, hsa-miR-1247, hsa-miR-381, hsa-miR-154, hsa-miR-433, hsa-miR-1244, hsa-miR-4485, hsa-miR-378e, hsa-miR-505, hsa-miR-376c, hsa-miR-1296, hsa-miR-29b-1*, hsa-miR-409-5p, hsa-miR-29c*, hsa-miR-34c-3p, hsa-miR-4646-5p, hsa-miR-99a*, hsa-miR-378g, hsa-miR-504, hsa-miR-584, hsa-miR-128, hsa-miR-30c-1*, hsa-miR-665, hsa-miR-4269, hsa-miR-493*, hsa-miR-328, hsa-miR-550a, hsa-miR-375, hsa-miR-493, hsa-miR-378d, hsa-miR-148a*, hsa-miR-615-3p, hsa-miR-431*, hsa-miR-378i, hsa-miR-422a, hsa-miR-331-5p, hsa-miR-378*, hsa-miR-148b, hsa-miR-601, hsa-miR-4288, hsa-miR-596, hsa-miR-10a, hsa-miR-200c*, hsa-miR-378b, hsa-miR-378f, hsa-miR-4257, hsa-miR-370, hsa-miR-1237, hsa-miR-3942-3p, hsa-miR-1269b, hsa-miR-4741, hsa-miR-4763-3p, hsa-miR-4704-5p, hsa-miR-1911*, hsa-miR-3621, hsa-miR-3612, hsa-miR-4436b-5p, hsa-miR-4734, hsa-miR-3185, hsa-miR-3910, hsa-miR-4727-3p, hsa-miR-155, hsa-miR-155*, hsa-miR-4529-3p, hsa-miR-3927, hsa-miR-3201, hsa-miR-4423-3p, hsa-miR-124 and hsa-miR-184;

3) hsa-miR-211, hsa-miR-29b, hsa-miR-4324, hsa-miR-143*, hsa-miR-1287, hsa-miR-4708-5p, hsa-miR-195*, hsa-miR-508-5p, hsa-miR-204, hsa-miR-96, hsa-let-7b*, hsa-miR-935, hsa-miR-675*, hsa-miR-149, hsa-miR-30a*, hsa-miR-1181, hsa-miR-506, hsa-miR-23c, hsa-miR-127-5p, hsa-miR-491-5p, hsa-miR-4776-5p, hsa-miR-601, hsa-miR-4530, hsa-miR-4773, hsa-miR-4717-3p, hsa-miR-4657, hsa-miR-4289, hsa-miR-4417, hsa-miR-4445*, hsa-miR-150, hsa-miR-146b-5p, hsa-miR-3175, hsa-miR-4646-5p, hsa-miR-3163, hsa-miR-4423-3p, hsa-miR-3128, hsa-miR-1244, hsa-miR-21*, hsa-miR-3201, hsa-miR-335

4) hsa-miR-223, hsa-miR-142-3p, hsa-miR-146b, hsa-miR-21, hsa-miR-155, hsa-miR-30b, hsa-miR-221, hsa-miR-141, hsa-miR-339-3p, hsa-miR-100, hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-199a, hsa-miR-125a-5p, mmu-miR-491, hsa-miR-489, hsa-miR-337-5p, hsa-miR-149, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a.

According to another particular aspect, the expression of one or more microRNAs is furthermore determined, said RNAs being selected from one of the groups consisting of a) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-4269, hsa-miR-1296, hsa-miR-34c-3p, hsa-miR-204, hsa-miR-504, hsa-miR-30c-1*, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-148b, hsa-miR-378g, hsa-miR-1238, hsa-miR-181a-2*, hsa-miR-187, hsa-miR-378d, hsa-miR-181d, hsa-miR-98, hsa-miR-4685-3p, hsa-miR-23b*, hsa-miR-3201, hsa-miR-4423-3p, hsa-miR-3128, hsa-miR-155, hsa-miR-3163, hsa-miR-146b-5p, hsa-miR-606, hsa-miR-150, hsa-miR-4776-5p, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p b) hsa-miR-223, hsa-miR-142-3p, hsa-miR-146b, hsa-miR-21, hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-125a-5p, mmu-miR-491, hsa-miR-127, hsa-miR-375, hsa-miR-101, hsa-miR- 296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a c) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-885-5p, hsa-miR-1287, hsa-miR-95, hsa-miR-376c, hsa-miR-195*, hsa-miR-4269, mmu-miR-499, hsa-miR-1296, hsa-miR-34c-3p, hsa-miR-204, hsa-miR-504, hsa-miR-30c-1*, hsa-miR-487b, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-491-5p, hsa-miR-148b, hsa-miR-378g, hsa-miR-125a-5p, hsa-miR-1238, hsa-miR-181a-2*, hsa-miR-187, hsa-miR-30c, hsa-miR-27a, hsa-miR-99a, hsa-miR-378d, hsa-miR-181d, hsa-miR-98, hsa-miR-4685-3p, hsa-miR-598, hsa-miR-23b*, hsa-miR-3201, hsa-miR-4423-3p, hsa-miR-223, hsa-miR-3128, hsa-miR-155, hsa-miR-3163, hsa-miR-146b-5p, hsa-miR-606, hsa-miR-150, hsa-miR-4776-5p, hsa-miR-142-3p, hsa-miR-21, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p d) hsa-miR-3201, hsa-miR-4423-3p, hsa-miR-3128, hsa-miR-3163, hsa-miR-606, hsa-miR-4776-5p, hsa-miR-635, hsa-miR-3124-5p, hsa-miR-4741, hsa-miR-4668-5p, hsa-miR-4763-3p, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p.

According to a particular aspect, the expression of one or more microRNAs is furthermore determined, said RNAs being selected from one of the groups consisting of hsa-miR-133a, hsa-miR-133b, hsa-miR-1, hsa-miR-486-3p, hsa-miR-34c-3p, hsa-miR-375 and hsa-miR-146b-5p.

According to a particular aspect, the expression of one or more microRNAs is furthermore determined, said RNAs, an increase in the expression of which in the sample relative to the controls indicates that the subject suffers from or is likely to suffer from rosacea, being selected from one of the groups consisting of 1) hsa-miR-4758-5p, hsa-miR-4665-5p, hsa-miR-149*, hsa-miR-548ac, hsa-miR-4507, hsa-miR-548a-3p, hsa-miR-4289, hsa-miR-4727-3p, hsa-miR-4468, hsa-miR-4463, hsa-miR-2861, hsa-miR-4773, hsa-miR-1825, hsa-miR-4651, hsa-miR-216b, hsa-miR-4689, hsa-miR-3152-3p, hsa-miR-4270, hsa-miR-1915, hsa-miR-4739, hsa-miR-4772-5p, hsa-miR-4687-3p, hsa-miR-4674, hsa-miR-4695-5p, hsa-miR-4439, hsa-miR-129-3p, hsa-miR-1469, hsa-miR-4659a-3p, hsa-miR-4799-3p, hsa-miR-4657, hsa-miR-4655-5p, hsa-miR-4745-5p, hsa-miR-4662b, hsa-miR-4707-5p, hsa-miR-3185, hsa-miR-4260, hsa-miR-4530, hsa-miR-4734, hsa-miR-1911*, hsa-miR-4417, hsa-miR-4763-3p, hsa-miR-4668-5p, hsa-miR-1281, hsa-miR-635, hsa-miR-4741, hsa-miR-3124-5p, hsa-miR-146b-3p, hsa-miR-4529-3p, hsa-miR-4776-5p, hsa-miR-150, hsa-miR-3927, hsa-miR-606, hsa-miR-146b-5p, hsa-miR-3163, hsa-miR-155, hsa-miR-371b-5p, hsa-miR-3128, hsa-miR-4423-3p, hsa-miR-335, hsa-miR-3201, hsa-miR-184

2) hsa-miR-1269b, hsa-miR-4741, hsa-miR-4763-3p, hsa-miR-4704-5p, hsa-miR-1911*, hsa-miR-3621, hsa-miR-3612, hsa-miR-4436b-5p, hsa-miR-4734, hsa-miR-3185, hsa-miR-3910, hsa-miR-4727-3p, hsa-miR-155, hsa-miR-155*, hsa-miR-4529-3p, hsa-miR-3927, hsa-miR-3201, hsa-miR-4423-3p, hsa-miR-124, hsa-miR-184;

3) hsa-miR-4776-5p, hsa-miR-601, hsa-miR-4530, hsa-miR-4773, hsa-miR-4717-3p, hsa-miR-4657, hsa-miR-4289, hsa-miR-4417, hsa-miR-4445*, hsa-miR-150, hsa-miR-146b-5p, hsa-miR-3175, hsa-miR-4646-5p, hsa-miR-3163, hsa-miR-4423-3p, hsa-miR-3128, hsa-miR-1244, hsa-miR-21*, hsa-miR-3201, hsa-miR-335

4) hsa-miR-223, hsa-miR-142-3p, hsa-miR-146b, hsa-miR-21, hsa-miR-155 a) hsa-miR-3201, hsa-miR-4423-3p, hsa-miR-3128, hsa-miR-155, hsa-miR-3163, hsa-miR-146b-5p, hsa-miR-606, hsa-miR-150, hsa-miR-4776-5p, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p b) hsa-miR-223, hsa-miR-142-3p, hsa-miR-146b, hsa-miR-21 c) hsa-miR-3201, hsa-miR-4423-3p, hsa-miR-223, hsa-miR-3128, hsa-miR-155, hsa-miR-3163, hsa-miR-146b-5p, hsa-miR-606, hsa-miR-150, hsa-miR-4776-5p, hsa-miR-142-3p, hsa-miR-21, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p d) hsa-miR-3201, hsa-miR-4423-3p, hsa-miR-3128, hsa-miR-3163, hsa-miR-606, hsa-miR-4776-5p, hsa-miR-635, hsa-miR-3124-5p, hsa-miR-4741, hsa-miR-4668-5p, hsa-miR-4763-3p, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p, hsa-miR-146b-5p According to yet another particular aspect, the expression of one or more microRNAs is furthermore determined, said RNAs, a decrease in the expression of which in the sample relative to the controls indicates that the subject suffers from or is likely to suffer from rosacea, being selected from one of the groups consisting of 1) hsa-miR-133a, hsa-miR-206, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-411, hsa-miR-4269, hsa-miR-328, hsa-miR-1296, hsa-miR-34c-3p, hsa-miR-204, hsa-miR-504, hsa-miR-30c-1*, hsa-miR-615-3p, hsa-miR-654-3p, hsa-miR-505, hsa-miR-508-5p, hsa-miR-409-5p, hsa-miR-338-5p, hsa-miR-433, hsa-miR-375, hsa-miR-935, hsa-let-7d*, hsa-miR-99a*, hsa-miR-128, hsa-miR-1290, hsa-miR-331-5p, hsa-miR-4730, hsa-miR-29c*, hsa-miR-455-5p, hsa-miR-377*, hsa-miR-378e, hsa-miR-584, hsa-miR-96, hsa-miR-30a*, hsa-miR-143*, hsa-miR-370, hsa-miR-148a*, hsa-miR-489, hsa-miR-506, hsa-let-7e*, hsa-miR-30e*, hsa-miR-4787-3p, hsa-let-7b*, hsa-miR-181c*, hsa-miR-513a-5p, hsa-miR-92a-1*, hsa-miR-337-5p, hsa-miR-1181, hsa-miR-1237, hsa-miR-3620, hsa-miR-485-5p, hsa-miR-23c, hsa-miR-18a*, hsa-miR-10a, hsamiR-139-3p, hsa-miR-493, hsa-miR-148b, hsa-miR-550a, hsa-miR-3147, hsa-miR-378g, hsa-miR-675*, hsa-miR-1238, hsa-miR-542-5p, hsa-miR-30c-2*, hsa-miR-125a-3p, hsa-miR-181a-2*, hsa-miR-1292, hsa-miR-187, hsa-miR-378*, hsa-miR-493*, hsa-miR-495, hsa-miR-557, hsa-miR-3909, hsa-miR-378d, hsa-miR-491-5p, hsa-miR-181d, hsa-miR-671-3p, hsa-miR-513c, hsa-miR-487b, hsa-miR-378b, hsa-miR-885-5p, hsa-miR-98, hsa-miR-29b-2*, hsa-miR-4685-3p, hsa-miR-3605-3p, hsa-miR-24-1*, hsa-miR-4649-3p, hsa-miR-3180-5p, hsa-miR-149, hsa-miR-23b*

2) hsa-miR-206, hsa-miR-133b, hsa-miR-133a, hsa-miR-1, hsa-miR-486-3p, hsa-miR-299-5p, hsa-miR-1247, hsa-miR-381, hsa-miR-154, hsa-miR-433, hsa-miR-1244, hsa-miR-4485, hsa-miR-378e, hsa-miR-505, hsa-miR-376c, hsa-miR-1296, hsa-miR-29b-1*, hsa-miR-409-5p, hsa-miR-29c*, hsa-miR-34c-3p, hsa-miR-4646-5p, hsa-miR-99a*, hsa-miR-378g, hsa-miR-504, hsa-miR-584, hsa-miR-128, hsa-miR-30c-1*, hsa-miR-665, hsa-miR-4269, hsa-miR-493*, hsa-miR-328, hsa-miR-550a, hsa-miR-375, hsa-miR-493, hsa-miR-378d, hsa-miR-148a*, hsa-miR-615-3p, hsa-miR-431*, hsa-miR-378i, hsa-miR-422a, hsa-miR-331-5p, hsa-miR-378*, hsa-miR-148b, hsa-miR-601, hsa-miR-4288, hsa-miR-596, hsa-miR-10a, hsa-miR-200c*, hsa-miR-378b, hsa-miR-378f, hsa-miR-4257, hsa-miR-370, hsa-miR-1237, hsa-miR-3942-3p 3) hsa-miR-211, hsa-miR-29b, hsa-miR-4324, hsa-miR-143*, hsa-miR-1287, hsa-miR-4708-5p, hsa-miR-195*, hsa-miR-508-5p, hsa-miR-204, hsa-miR-96, hsa-let-7b*, hsa-miR-935, hsa-miR-675*, hsa-miR-149, hsa-miR-30a*, hsa-miR-1181, hsa-miR-506, hsa-miR-23c, hsa-miR-127-5p, hsa-miR-491-5p 4) hsa-miR-30b, hsa-miR-221, hsa-miR-141, hsa-miR-339-3p, hsa-miR-100, hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-199a, hsa-miR-125a-5p, mmu-miR-491, hsa-miR-489, hsa-miR-337-5p, hsa-miR-149, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a.

a) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-4269, hsa-miR-1296, hsa-miR-34c-3p, hsa-miR-204, hsa-miR-504, hsa-miR-30c-1*, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-148b, hsa-miR-378g, hsa-miR-1238, hsa-miR-181a-2*, hsa-miR-187, hsa-miR-378d, hsa-miR-181d, hsa-miR-98, hsa-miR-4685-3p, hsa-miR-23b* b) hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-125a-5p, mmu-miR-491, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a c) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-885-5p, hsa-miR-1287, hsa-miR-95, hsa-miR-376c, hsa-miR-195*, hsa-miR-4269, mmu-miR-499, hsa-miR-1296, hsa-miR-34c-3p, hsa-miR-204, hsa-miR-504, hsa-miR-30c-1*, hsa-miR-487b, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-491-5p, hsa-miR-148b, hsa-miR-378g, hsa-miR-125a-5p, hsa-miR-1238, hsa-miR-181a-2*, hsa-miR-187, hsa-miR-30c, hsa-miR-27a, hsa-miR-99a, hsa-miR-378d, hsa-miR-181d, hsa-miR-98, hsa-miR-4685-3p, hsa-miR-598, hsa-miR-23b*

5) hsa-miR-133a, hsa-miR-133b, hsa-miR-1, hsa-miR-486-3p, hsa-miR-34c-3p, hsa-miR-375.

The detection or the quantification of the biological sample(s) from the control subject(s) may be concomitant with that carried out for the patient sample or may come from data collected earlier and available, for example, in a database.

In the methods according to the invention, microRNA expression may be detected or quantified according to methods well known to persons skilled in the art, for example by quantitative RT-PCR and/or hybridization techniques, for example using a labeled probe or a chip.

Another object of the invention relates to a method for monitoring or determining the efficacy of a rosacea treatment in a subject comprising determining in a sample from said subject the expression of one or more microRNAs selected from one of the groups consisting of hsa-miR-3201, hsa-miR-4423-3p, hsa-miR-3128, hsa-miR-3163, hsa-miR-606, hsa-miR-4776-5p and hsa-miR-635, the decrease in the expression of one or more microRNAs at the conclusion of or during the treatment indicates the efficacy of the treatment.

Therapeutic Applications

It is also possible to target the regulation of these microRNAs to treat or prevent rosacea; the molecule used for the treatment is a molecule for decreasing or suppressing dysregulation of the expression of one or more microRNAs differentially expressed in subjects suffering from rosacea. In particular, microRNAs underexpressed in subjects suffering from rosacea may be used to treat rosacea by administering same. Alternatively, when microRNAs are overexpressed in subjects suffering from rosacea, the treatment will be directed at increasing the expression of the target gene, for example by blocking the effect of these microRNAs.

Described herein is a pharmaceutical composition comprising one or more identified microRNAs and the use of same to treat rosacea or to prepare a drug intended to treat rosacea. Preferably, the composition further includes one or more pharmaceutically acceptable excipients and/or carriers. The present invention also relates to an expression vector comprising a nucleotide sequence encoding one or more identified microRNAs or precursors thereof and the use of same to treat rosacea or to prepare a drug intended to treat rosacea. Preferably, the identified microRNAs are selected from microRNAs underexpressed in patients suffering from rosacea.

The microRNA(s) of interest are as described herein.

It is proposed to use to treat rosacea a molecule or a combination of molecules, which may increase the expression of one or more microRNAs described herein, or precursors of these microRNAs, or a nucleic acid encoding said microRNA(s) or precursors thereof, or an analog, derivative or modified form of the microRNA(s) retaining its or their activity.

Conversely, said molecule or combination of molecules may be an inhibitor of the microRNA(s), preferably a sense or antisense oligonucleotide capable of hybridizing to said microRNA(s), thus inhibiting the production and/or the activity of the microRNA(s) or increasing the depletion of the microRNA(s).

It is also envisaged to perform a screening to identify novel drugs for treating rosacea, wherein the candidate molecules will be tested as to their capacity to fully or partially restore the expression of dysregulated microRNAs in subjects suffering from rosacea and the molecules having the desired effect will be selected.

Thus described herein is a method for screening molecules useful in the treatment of rosacea, preferably type II rosacea, comprising a) contacting a cell with a test molecule, b) determining the expression of the following seven microRNAs: hsa-miR-3201, hsa-miR-4423-3p, hsa-miR-3128, hsa-miR-3163, hsa-miR-606, hsa-miR-4776-5p and hsa-miR-635, or capable of modulating the expression of one or of said microRNA(s) and c) selecting the test molecule if it increases or decreases the expression or the activity of one or more of said microRNAs.

Further described herein is the use of a molecule or a combination of molecules to treat rosacea, preferably type II rosacea, said molecule or combination of molecules making it possible to decrease the expression of at least one of the following seven microRNAs: hsa-miR-3201, hsa-miR-4423-3p, hsa-miR-3128, hsa-miR-3163, hsa-miR-606, hsa-miR-4776-5p and hsa-miR-635, or capable of modulating the expression of one or more microRNAs described herein.

Typically, the expression or activity of a microRNA is analyzed and compared in the presence and in the absence of the test molecule.

The following experimental section illustrates the invention without limiting it scope.

EXAMPLES

Introduction

This is a clinical study wherein the samples, 3 mm skin biopsies taken from the nasal fold, come from three groups of individuals:
- 7 healthy volunteer subjects (HV) used as controls to establish a differential with the pathology,
- 8 subjects having ETR (RI),
- 9 subjects having PPR (RII).

The inventors were interested in characterizing the miRNome in erythematotelangiectatic rosacea (subtype I) and papulopustular rosacea (subtype II).

To this end, the Affymetrix technology was used for the large-scale study of microRNAs.

Concerning the statistical analyses, the large-scale expression data were filtered on the species *Homo sapiens* then normalized by Robust Multiarray/Multichip Average (RMA). An expression level filter was then applied. Next, the normalized data were compared statistically by differential analysis in order to establish a list of microRNAs significantly and specifically modulated in lesional skin (affected subjects) relative to healthy skin (healthy subjects). Lastly, the biological interpretation was made starting with a list of modulated microRNAs in papulopustular rosacea using the Ingenuity Pathway Analysis software, by interconnecting the data from the subject transcriptome study (mRNA expression profiles).

Characterization of the pathology's miRNome proceeds first by a large-scale study, using Affymetrix miRNA 3.0 chips, in order to establish microRNA expression profiles. A detailed analysis made it possible to establish the work method to be adopted: expression level filtering, data normalization, then differential analysis.

To supplement the miRNome data, transcriptome data (mRNA expression profiles) produced by this same study were linked.

Although all the samples were processed, few microRNAs of interest proved to be differentially expressed in RI relative to healthy skin. Hence, the project focused on the study of microRNAs for discriminating subjects affected with type II (papulopustular) rosacea from subjects not having rosacea. A list of 92 microRNAs was shown to be significantly differentially expressed in RII vs HV. With the aim of discovering potential microRNA biomarkers, microRNA expression was compared in three skin pathologies: psoriasis, acne and rosacea. Interestingly, we observed a majority of specifically modulated microRNAs in each pathology, confirming the characteristic signatures of these small regulatory RNAs. In this project, 7 microRNA biomarkers of rosacea were revealed.

Results

Large-Scale Study of microRNAs a) Quality Control of the Affymetrix miRNA 3.0 Chip After RMA normalization of the experimental data, a series of quality controls is carried out. Included are:

Control of average background noise with $$\frac{\text{max noise value}}{\text{min noise value}} < 3$$

for the 24 samples.

Five control oligonucleotides injected into the RNA samples before the RNA biotinylation step show an average intensity greater than 10; these controls validate the polyadenylation and ligation steps.

Four targets injected at the time of the step of hybridizing the RNAs to the chip probes have the expected profile: $\text{Intensity}_{bioB} < \text{Intensity}_{bioC} < \text{Intensity}_{bioD} < \text{Intensity}_{Cre}$; these controls confirm that the hybridization step was carried out satisfactorily.

Finally, principal component analysis is used to detect possible aberrant samples and to observe possible sample groupings in a very comprehensive manner. No sample leaves the confidence circle. Hence, we were able to retain all the study samples.

b) Robust MultiArray Average (RMA) Normalization

RMA normalization was carried out:

On all the target sets present on the chip (25,119 identifiers).

On all the human target sets (5683 identifiers). Normalization was then performed using Expression Console by filtering the expression data on the species *Homo sapiens*.

These normalized data were then compared by means of a differential analysis comparing RII individuals with healthy individuals. As these two analyses showed very small differences, the following analyses were performed on the data normalized in Expression Console on humans (5683 identifiers). Furthermore, RI versus HV and RII versus RI differential analyses revealed fewer modulated microRNAs, which is why the following analyses focused on differential analysis of the miRNome of affected individuals (RII) versus the miRNome of healthy individuals (HV) with 29 significantly modulated microRNAs without filtering expression level.

TABLE 1

|  | RI vs HV | RII vs HV | RII vs RI |  |
|---|---|---|---|---|
| Number of modulated microRNAs* with \|Fold\| ≥ 1.5 and p-value ≤ 0.05 | 74 | 160 | 40 | 5 |
| Number of modulated microRNAs** with \|Fold\| ≥ 1.5 and FDR ≤ 0.05 | 1 | 29 | 1 |  |

*mature human microRNAs with |Fold| ≥ 1.5 and p-value ≤ 0.05 (without FDR correction) and without filtering expression level before differential analysis.
**mature human microRNAs with |Fold| ≥ 1.5 and FDR ≤ 0.05 without filtering expression level before differential analysis.

TABLE 2

List of 74 modulated mature microRNAs (|fold| ≥1.5 and raw p-value ≤0.05) in the RI vs HV differential analysis (Blume rosacea study: GRDS0050) starting with 3391 Affymetrix identifiers

| Affymetrix id | FoldChange | RawPValue | FDR_BH | mean expression RI | mean expression HV |
|---|---|---|---|---|---|
| hsa-miR-206 | −36.5 | 2.4E−02 | 4.6E−01 | 33 | 1213 |
| hsa-miR-133b | −24.8 | 7.9E−03 | 3.5E−01 | 19 | 466 |
| hsa-miR-133a | −23.6 | 2.4E−02 | 4.6E−01 | 24 | 562 |
| hsa-miR-1 | −6.2 | 9.0E−03 | 3.5E−01 | 5 | 31 |
| hsa-miR-486-3p | −3.9 | 1.3E−02 | 3.9E−01 | 12 | 48 |
| hsa-miR-299-5p | −3.2 | 2.6E−02 | 4.8E−01 | 11 | 36 |
| hsa-miR-1247 | −3.0 | 1.1E−03 | 2.0E−01 | 10 | 29 |
| hsa-miR-381 | −2.9 | 2.2E−02 | 4.6E−01 | 18 | 52 |
| hsa-miR-154 | −2.9 | 2.4E−05 | 4.1E−02 | 10 | 28 |
| hsa-miR-433 | −2.4 | 1.7E−03 | 2.0E−01 | 6 | 14 |
| hsa-miR-1244 | −2.4 | 7.1E−03 | 3.3E−01 | 7 | 15 |
| hsa-miR-4485 | −2.3 | 5.8E−03 | 3.2E−01 | 21 | 48 |
| hsa-miR-378e | −2.3 | 2.0E−03 | 2.0E−01 | 48 | 109 |
| hsa-miR-505 | −2.2 | 8.5E−03 | 3.5E−01 | 12 | 26 |
| hsa-miR-376c | −2.2 | 3.1E−02 | 4.9E−01 | 5 | 11 |
| hsa-miR-1296 | −2.2 | 1.1E−03 | 2.0E−01 | 8 | 17 |
| hsa-miR-29b-1* | −2.2 | 3.0E−02 | 4.9E−01 | 15 | 33 |
| hsa-miR-409-5p | −2.1 | 1.5E−02 | 4.2E−01 | 11 | 22 |
| hsa-miR-29c* | −2.1 | 1.2E−02 | 3.8E−01 | 12 | 25 |
| hsa-miR-34c-3p | −2.1 | 6.0E−04 | 1.5E−01 | 7 | 13 |
| hsa-miR-4646-5p | −2.0 | 6.0E−04 | 1.5E−01 | 7 | 14 |
| hsa-miR-99a* | −2.0 | 1.7E−02 | 4.2E−01 | 14 | 28 |
| hsa-miR-378g | −2.0 | 1.0E−04 | 1.2E−01 | 144 | 281 |
| hsa-miR-504 | −1.9 | 2.1E−02 | 4.5E−01 | 8 | 16 |
| hsa-miR-584 | −1.9 | 5.9E−03 | 3.2E−01 | 13 | 24 |
| hsa-miR-128 | −1.9 | 8.0E−03 | 3.5E−01 | 52 | 98 |
| hsa-miR-30c-1* | −1.8 | 9.3E−03 | 3.5E−01 | 9 | 17 |
| hsa-miR-665 | −1.8 | 3.1E−02 | 4.9E−01 | 8 | 15 |
| hsa-miR-4269 | −1.8 | 4.0E−03 | 2.9E−01 | 26 | 46 |
| hsa-miR-493* | −1.8 | 8.0E−04 | 1.8E−01 | 2 | 4 |
| hsa-miR-328 | −1.8 | 8.8E−03 | 3.5E−01 | 16 | 28 |
| hsa-miR-550a | −1.8 | 2.4E−02 | 4.6E−01 | 6 | 10 |
| hsa-miR-375 | −1.7 | 1.6E−02 | 4.2E−01 | 29 | 50 |
| hsa-miR-493 | −1.7 | 1.9E−02 | 4.3E−01 | 3 | 5 |
| hsa-miR-378d | −1.7 | 1.0E−04 | 1.2E−01 | 270 | 464 |
| hsa-miR-148a* | −1.7 | 1.4E−02 | 4.1E−01 | 5 | 9 |
| hsa-miR-615-3p | −1.7 | 7.0E−03 | 3.3E−01 | 3 | 5 |
| hsa-miR-431* | −1.7 | 2.0E−03 | 2.0E−01 | 2 | 4 |
| hsa-miR-378i | −1.7 | 4.0E−04 | 1.3E−01 | 483 | 817 |
| hsa-miR-422a | −1.7 | 3.0E−04 | 1.3E−01 | 480 | 810 |
| hsa-miR-331-5p | −1.7 | 5.0E−02 | 5.5E−01 | 7 | 12 |
| hsa-miR-378* | −1.7 | 9.2E−03 | 3.5E−01 | 161 | 267 |
| hsa-miR-148b | −1.7 | 1.6E−03 | 2.0E−01 | 39 | 64 |
| hsa-miR-601 | −1.6 | 2.0E−04 | 1.3E−01 | 2 | 3 |
| hsa-miR-4288 | −1.6 | 3.5E−03 | 2.8E−01 | 4 | 6 |
| hsa-miR-596 | −1.6 | 4.9E−02 | 5.5E−01 | 4 | 6 |
| hsa-miR-10a | −1.6 | 4.7E−02 | 5.5E−01 | 5 | 8 |
| hsa-miR-200c* | −1.6 | 5.0E−02 | 5.5E−01 | 8 | 13 |
| hsa-miR-378b | −1.6 | 1.1E−02 | 3.7E−01 | 15 | 23 |
| hsa-miR-378f | −1.6 | 1.2E−03 | 2.0E−01 | 641 | 1002 |
| hsa-miR-4257 | −1.5 | 1.7E−02 | 4.2E−01 | 3 | 4 |
| hsa-miR-370 | −1.5 | 9.6E−03 | 3.5E−01 | 15 | 23 |
| hsa-miR-1237 | −1.5 | 2.7E−02 | 4.8E−01 | 3 | 5 |
| hsa-miR-3942-3p | 1.5 | 1.5E−02 | 4.2E−01 | 4 | 3 |
| hsa-miR-1269b | 1.5 | 2.3E−03 | 2.1E−01 | 3 | 2 |
| hsa-miR-4741 | 1.5 | 1.9E−02 | 4.3E−01 | 439 | 288 |
| hsa-miR-4763-3p | 1.5 | 1.8E−02 | 4.3E−01 | 1889 | 1235 |
| hsa-miR-4704-5p | 1.5 | 3.6E−02 | 5.1E−01 | 6 | 4 |

TABLE 2-continued

List of 74 modulated mature microRNAs (|fold| ≥1.5
and raw p-value ≤0.05) in the RI vs HV differential analysis
(Blume rosacea study: GRDS0050) starting with 3391 Affymetrix identifiers

| Affymetrix id | FoldChange | RawPValue | FDR_BH | mean expression RI | mean expression HV |
|---|---|---|---|---|---|
| hsa-miR-1911* | 1.5 | 3.5E-02 | 5.1E-01 | 4 | 3 |
| hsa-miR-3621 | 1.5 | 4.1E-02 | 5.3E-01 | 809 | 525 |
| hsa-miR-3612 | 1.5 | 5.4E-03 | 3.2E-01 | 5 | 3 |
| hsa-miR-4436b-5p | 1.5 | 4.3E-02 | 5.4E-01 | 67 | 44 |
| hsa-miR-4734 | 1.6 | 1.3E-02 | 4.1E-01 | 1326 | 855 |
| hsa-miR-3185 | 1.6 | 1.8E-02 | 4.3E-01 | 743 | 479 |
| hsa-miR-3910 | 1.7 | 6.3E-03 | 3.3E-01 | 16 | 10 |
| hsa-miR-4727-3p | 1.7 | 1.9E-03 | 2.0E-01 | 13 | 8 |
| hsa-miR-155 | 1.7 | 4.6E-02 | 5.5E-01 | 683 | 397 |
| hsa-miR-155* | 1.8 | 1.8E-02 | 4.3E-01 | 8 | 5 |
| hsa-miR-4529-3p | 1.9 | 4.7E-02 | 5.5E-01 | 57 | 30 |
| hsa-miR-3927 | 1.9 | 2.8E-02 | 4.9E-01 | 10 | 5 |
| hsa-miR-3201 | 2.0 | 1.6E-02 | 4.2E-01 | 102 | 51 |
| hsa-miR-4423-3p | 2.3 | 3.9E-03 | 2.9E-01 | 20 | 9 |
| hsa-miR-124 | 6.7 | 2.1E-03 | 2.0E-01 | 28 | 4 |
| hsa-miR-184 | 15.9 | 9.0E-04 | 1.9E-01 | 39 | 2 |

TABLEAU 3

List of 160 modulated mature microRNAs (|fold| ≥1.5
and raw p-value ≤0.05) in the RII vs HV differential analysis
(Blume rosacea study: GRDS0050) starting with 3391
Affymetrix identifiers

| Affymetrix id | Fold Change | RawPValue | FDR_BH | mean expression HV | mean expression RII |
|---|---|---|---|---|---|
| hsa-miR-133a | -45.81 | 6.4E-03 | 1.2E-01 | 562 | 12 |
| hsa-miR-206 | -43.52 | 1.6E-02 | 1.9E-01 | 1213 | 28 |
| hsa-miR-133b | -38.97 | 2.4E-03 | 8.1E-02 | 466 | 12 |
| hsa-miR-1 | -9.71 | 1.4E-03 | 6.7E-02 | 31 | 3 |
| hsa-miR-299-5p | -5.11 | 2.5E-03 | 8.1E-02 | 36 | 7 |
| hsa-miR-486-3p | -4.67 | 4.8E-03 | 1.1E-01 | 48 | 10 |
| hsa-miR-381 | -3.54 | 6.5E-03 | 1.2E-01 | 52 | 15 |
| hsa-miR-4324 | -3.53 | 7.0E-04 | 4.4E-02 | 20 | 6 |
| hsa-miR-154 | -3.49 | 1.6E-06 | 2.3E-03 | 28 | 8 |
| hsa-miR-1247 | -3.44 | 3.0E-04 | 2.6E-02 | 29 | 9 |
| hsa-miR-1287 | -3.28 | 8.0E-04 | 4.8E-02 | 14 | 4 |
| hsa-miR-376c | -2.81 | 5.7E-03 | 1.1E-01 | 11 | 4 |
| hsa-miR-195* | -2.78 | 5.0E-04 | 3.7E-02 | 16 | 6 |
| hsa-miR-411 | -2.74 | 2.7E-02 | 2.4E-01 | 19 | 7 |
| hsa-miR-4269 | -2.63 | 1.5E-05 | 3.4E-03 | 46 | 18 |
| hsa-miR-328 | -2.59 | 6.0E-05 | 9.7E-03 | 28 | 11 |
| hsa-miR-1296 | -2.53 | 2.0E-04 | 1.8E-02 | 17 | 7 |
| hsa-miR-34c-3p | -2.53 | 2.5E-05 | 5.2E-03 | 13 | 5 |
| hsa-miR-204 | -2.50 | 1.1E-03 | 5.8E-02 | 9 | 4 |
| hsa-miR-504 | -2.48 | 2.1E-03 | 7.4E-02 | 16 | 6 |
| hsa-miR-30c-1* | -2.47 | 2.0E-04 | 2.3E-02 | 17 | 7 |
| hsa-miR-615-3p | -2.41 | 4.7E-05 | 8.3E-03 | 5 | 2 |
| hsa-miR-654-3p | -2.37 | 7.9E-03 | 1.3E-01 | 16 | 7 |
| hsa-miR-505 | -2.34 | 4.6E-03 | 1.1E-01 | 26 | 11 |
| hsa-miR-508-5p | -2.33 | 1.0E-04 | 1.6E-02 | 13 | 6 |
| hsa-miR-409-5p | -2.31 | 5.4E-03 | 1.1E-01 | 22 | 10 |
| hsa-miR-338-5p | -2.25 | 3.2E-02 | 2.5E-01 | 14 | 6 |
| hsa-miR-433 | -2.25 | 2.9E-03 | 8.9E-02 | 14 | 6 |
| hsa-miR-375 | -2.22 | 1.0E-03 | 5.2E-02 | 50 | 23 |
| hsa-miR-935 | -2.19 | 8.0E-04 | 4.8E-02 | 9 | 4 |
| hsa-let-7d* | -2.15 | 1.2E-02 | 1.7E-01 | 14 | 7 |
| hsa-miR-99a* | -2.13 | 8.9E-03 | 1.4E-01 | 28 | 13 |
| hsa-miR-128 | -2.13 | 1.8E-03 | 7.2E-02 | 98 | 46 |
| hsa-miR-1290 | -2.11 | 1.9E-02 | 2.0E-01 | 104 | 49 |
| hsa-miR-331-5p | -2.11 | 5.6E-03 | 1.1E-01 | 12 | 6 |
| hsa-miR-4730 | -2.10 | 2.0E-02 | 2.1E-01 | 15 | 7 |
| hsa-miR-29c* | -2.08 | 9.9E-03 | 1.5E-01 | 25 | 12 |
| hsa-miR-455-5p | -2.04 | 1.7E-02 | 2.0E-01 | 12 | 6 |
| hsa-miR-377* | -1.98 | 4.2E-02 | 3.0E-01 | 7 | 4 |
| hsa-miR-378e | -1.98 | 7.2E-03 | 1.3E-01 | 109 | 55 |
| hsa-miR-584 | -1.96 | 3.9E-03 | 1.0E-01 | 24 | 12 |
| hsa-miR-96 | -1.93 | 1.1E-02 | 1.6E-01 | 6 | 3 |
| hsa-miR-30a* | -1.92 | 1.1E-05 | 3.3E-03 | 164 | 85 |
| hsa-miR-143* | -1.92 | 4.2E-02 | 3.0E-01 | 15 | 8 |
| hsa-miR-370 | -1.91 | 2.0E-04 | 1.8E-02 | 23 | 12 |
| hsa-miR-148a* | -1.88 | 3.4E-02 | 9.3E-02 | 9 | 5 |
| hsa-miR-489 | -1.86 | 5.2E-03 | 1.1E-01 | 53 | 29 |
| hsa-miR-506 | -1.85 | 1.1E-02 | 1.6E-01 | 5 | 3 |
| hsa-let-7e* | -1.84 | 1.6E-03 | 6.7E-02 | 4 | 2 |
| hsa-miR-30e* | -1.83 | 5.0E-03 | 1.1E-01 | 62 | 34 |
| hsa-miR-4787-3p | -1.81 | 1.3E-02 | 1.7E-01 | 11 | 6 |
| hsa-let-7b* | -1.80 | 7.2E-03 | 1.3E-01 | 11 | 6 |
| hsa-miR-181c* | -1.80 | 9.6E-03 | 1.5E-01 | 8 | 4 |
| hsa-miR-513a-5p | -1.79 | 4.0E-02 | 2.9E-01 | 28 | 15 |
| hsa-miR-92a-1* | -1.79 | 2.4E-02 | 2.3E-01 | 30 | 17 |
| hsa-miR-337-5p | -1.79 | 2.3E-03 | 7.9E-02 | 35 | 19 |
| hsa-miR-1181 | -1.77 | 5.9E-03 | 1.2E-01 | 12 | 7 |
| hsa-miR-1237 | -1.75 | 3.3E-02 | 9.1E-02 | 5 | 3 |
| hsa-miR-3620 | -1.75 | 2.8E-02 | 2.4E-01 | 8 | 5 |
| hsa-miR-485-5p | -1.74 | 1.9E-03 | 7.4E-02 | 23 | 13 |
| hsa-miR-23c | -1.74 | 4.3E-03 | 1.0E-01 | 79 | 45 |
| hsa-miR-18a* | -1.74 | 3.3E-02 | 2.6E-01 | 23 | 13 |
| hsa-miR-10a | -1.74 | 1.9E-02 | 2.0E-01 | 8 | 5 |
| hsa-miR-139-3p | -1.73 | 1.2E-02 | 1.7E-01 | 31 | 18 |
| hsa-miR-493 | -1.72 | 1.8E-02 | 2.0E-01 | 5 | 3 |
| hsa-miR-148b | -1.71 | 7.0E-04 | 4.6E-02 | 64 | 37 |
| hsa-miR-550a | -1.70 | 2.7E-02 | 2.4E-01 | 10 | 6 |
| hsa-miR-3147 | -1.70 | 1.2E-02 | 1.7E-01 | 16 | 9 |
| hsa-miR-378g | -1.69 | 1.2E-03 | 6.2E-02 | 281 | 166 |
| hsa-miR-675* | -1.66 | 2.5E-02 | 2.3E-01 | 6 | 4 |
| hsa-miR-1238 | -1.66 | 6.0E-03 | 1.2E-01 | 10 | 6 |
| hsa-miR-542-5p | -1.66 | 3.4E-02 | 2.6E-01 | 8 | 5 |
| hsa-miR-30c-2* | -1.65 | 8.6E-03 | 1.4E-01 | 22 | 13 |
| hsa-miR-125a-3p | -1.65 | 7.3E-03 | 1.3E-01 | 34 | 20 |
| hsa-miR-181a-2* | -1.65 | 2.9E-03 | 8.9E-02 | 155 | 94 |
| hsa-miR-1292 | -1.64 | 4.0E-02 | 2.9E-01 | 11 | 7 |
| hsa-miR-187 | -1.63 | 4.3E-03 | 1.0E-01 | 56 | 35 |
| hsa-miR-378* | -1.63 | 1.1E-02 | 1.6E-01 | 267 | 164 |
| hsa-miR-493* | -1.61 | 2.9E-03 | 8.9E-02 | 4 | 3 |
| hsa-miR-495 | -1.61 | 4.0E-02 | 2.9E-01 | 5 | 3 |
| hsa-miR-557 | -1.60 | 2.7E-02 | 2.4E-01 | 10 | 7 |
| hsa-miR-3909 | -1.59 | 2.9E-02 | 2.4E-01 | 4 | 2 |

TABLEAU 3-continued

List of 160 modulated mature microRNAs (|fold| ≥1.5 and raw p-value ≤0.05) in the RII vs HV differential analysis (Blume rosacea study: GRDS0050) starting with 3391 Affymetrix identifiers

| Affymetrix id | Fold Change | RawPValue | FDR_BH | mean expression HV | mean expression RII |
|---|---|---|---|---|---|
| hsa-miR-378d | −1.58 | 6.0E−04 | 4.1E−02 | 464 | 295 |
| hsa-miR-491-5p | −1.57 | 9.3E−03 | 1.5E−01 | 38 | 24 |
| hsa-miR-181d | −1.57 | 1.7E−02 | 7.1E−02 | 73 | 47 |
| hsa-miR-671-3p | −1.57 | 3.7E−02 | 2.8E−01 | 11 | 7 |
| hsa-miR-513c | −1.56 | 4.7E−02 | 3.2E−01 | 6 | 4 |
| hsa-miR-487b | −1.56 | 1.2E−02 | 1.6E−01 | 157 | 101 |
| hsa-miR-378b | −1.56 | 1.0E−02 | 1.5E−01 | 23 | 15 |
| hsa-miR-885-5p | −1.54 | 5.0E−02 | 3.3E−01 | 41 | 26 |
| hsa-miR-98 | −1.54 | 5.2E−03 | 1.1E−01 | 74 | 48 |
| hsa-miR-29b-2* | −1.54 | 8.7E−03 | 1.4E−01 | 61 | 40 |
| hsa-miR-4685-3p | −1.53 | 5.2E−03 | 1.1E−01 | 5 | 3 |
| hsa-miR-3605-3p | −1.52 | 1.2E−02 | 1.6E−01 | 4 | 2 |
| hsa-miR-24-1* | −1.52 | 3.2E−02 | 2.5E−01 | 4 | 3 |
| hsa-miR-4649-3p | −1.51 | 1.7E−02 | 1.9E−01 | 7 | 5 |
| hsa-miR-3180-5p | −1.51 | 2.1E−02 | 7.4E−02 | 5 | 3 |
| hsa-miR-149 | −1.50 | 2.8E−02 | 2.4E−01 | 595 | 396 |
| hsa-miR-23b* | −1.50 | 4.9E−03 | 1.1E−01 | 56 | 37 |
| hsa-miR-4758-5p | 1.50 | 2.4E−02 | 2.3E−01 | 195 | 293 |
| hsa-miR-4665-5p | 1.50 | 1.3E−02 | 1.7E−01 | 132 | 198 |
| hsa-miR-149* | 1.50 | 3.0E−02 | 2.5E−01 | 1169 | 1759 |
| hsa-miR-548ac | 1.51 | 4.7E−02 | 3.2E−01 | 15 | 23 |
| hsa-miR-4507 | 1.51 | 1.5E−02 | 1.8E−01 | 221 | 334 |
| hsa-miR-548a-3p | 1.51 | 3.8E−02 | 1.0E−01 | 23 | 35 |
| hsa-miR-4289 | 1.52 | 2.5E−02 | 2.4E−01 | 3 | 5 |
| hsa-miR-4727-3p | 1.53 | 7.2E−03 | 1.3E−01 | 8 | 12 |
| hsa-miR-4468 | 1.54 | 8.7E−05 | 1.2E−02 | 2 | 3 |
| hsa-miR-4463 | 1.54 | 4.2E−02 | 2.9E−01 | 622 | 956 |
| hsa-miR-2861 | 1.54 | 9.8E−02 | 1.5E−01 | 3594 | 5552 |
| hsa-miR-4773 | 1.55 | 2.0E−02 | 2.1E−01 | 8 | 12 |
| hsa-miR-1825 | 1.57 | 4.6E−02 | 3.1E−01 | 53 | 84 |
| hsa-miR-4651 | 1.58 | 1.1E−02 | 1.6E−01 | 567 | 893 |
| hsa-miR-216b | 1.58 | 4.1E−02 | 1.0E−01 | 3 | 5 |
| hsa-miR-4689 | 1.59 | 3.1E−02 | 2.5E−01 | 239 | 378 |
| hsa-miR-3152-3p | 1.59 | 4.6E−02 | 3.1E−01 | 7 | 12 |
| hsa-miR-4270 | 1.60 | 8.7E−03 | 1.4E−01 | 695 | 1111 |
| hsa-miR-1915 | 1.60 | 3.0E−02 | 8.9E−02 | 3941 | 6301 |
| hsa-miR-4739 | 1.62 | 2.7E−03 | 8.5E−02 | 753 | 1221 |
| hsa-miR-4772-5p | 1.64 | 1.2E−02 | 1.7E−01 | 3 | 5 |
| hsa-miR-4687-3p | 1.65 | 2.0E−04 | 1.8E−02 | 2168 | 3569 |
| hsa-miR-4674 | 1.65 | 3.0E−03 | 8.9E−02 | 388 | 640 |
| hsa-miR-4695-5p | 1.65 | 1.0E−03 | 5.2E−02 | 325 | 537 |
| hsa-miR-4439 | 1.65 | 3.2E−02 | 2.5E−01 | 4 | 6 |
| hsa-miR-129-3p | 1.66 | 2.2E−02 | 2.2E−01 | 6 | 9 |
| hsa-miR-1469 | 1.66 | 6.0E−04 | 4.0E−02 | 2171 | 3606 |
| hsa-miR-4659a-3p | 1.66 | 5.0E−04 | 3.7E−02 | 2 | 4 |
| hsa-miR-4799-3p | 1.66 | 3.5E−02 | 2.6E−01 | 3 | 5 |
| hsa-miR-4657 | 1.68 | 7.8E−03 | 1.3E−01 | 8 | 14 |
| hsa-miR-4655-5p | 1.68 | 8.7E−03 | 1.4E−01 | 47 | 79 |
| hsa-miR-4745-5p | 1.69 | 3.0E−03 | 8.9E−02 | 1374 | 2321 |
| hsa-miR-4662b | 1.70 | 2.4E−03 | 8.0E−02 | 2 | 4 |
| hsa-miR-4707-5p | 1.70 | 4.6E−03 | 1.1E−01 | 903 | 1535 |
| hsa-miR-3185 | 1.71 | 4.4E−03 | 1.1E−01 | 479 | 816 |
| hsa-miR-4260 | 1.71 | 3.6E−02 | 9.8E−02 | 3 | 6 |
| hsa-miR-4530 | 1.74 | 4.3E−03 | 1.0E−01 | 786 | 1371 |
| hsa-miR-4734 | 1.75 | 2.0E−02 | 7.4E−02 | 855 | 1495 |
| hsa-miR-1911* | 1.76 | 5.9E−02 | 1.2E−01 | 3 | 5 |
| hsa-miR-4417 | 1.77 | 4.6E−03 | 1.1E−01 | 32 | 56 |
| hsa-miR-4763-3p | 1.77 | 1.9E−03 | 7.4E−02 | 1235 | 2182 |
| hsa-miR-4668-5p | 1.78 | 3.0E−04 | 2.5E−02 | 1388 | 2476 |
| hsa-miR-1281 | 1.82 | 1.8E−02 | 2.0E−01 | 115 | 210 |
| hsa-miR-635 | 1.85 | 1.6E−03 | 6.7E−02 | 8 | 14 |
| hsa-miR-4741 | 1.86 | 9.0E−04 | 5.0E−02 | 288 | 537 |
| hsa-miR-3124-5p | 1.89 | 2.0E−03 | 7.4E−02 | 46 | 88 |
| hsa-miR-146b-3p | 1.91 | 3.8E−02 | 2.8E−01 | 3 | 7 |
| hsa-miR-4529-3p | 1.93 | 3.7E−02 | 2.7E−01 | 30 | 58 |
| hsa-miR-4776-5p | 2.14 | 7.5E−06 | 3.2E−03 | 8 | 17 |
| hsa-miR-150 | 2.15 | 3.1E−03 | 9.0E−02 | 586 | 1258 |
| hsa-miR-3927 | 2.17 | 8.6E−03 | 1.4E−01 | 5 | 11 |
| hsa-miR-606 | 2.18 | 3.2E−02 | 9.1E−02 | 3 | 7 |
| hsa-miR-146b-5p | 2.32 | 3.0E−04 | 2.5E−02 | 183 | 423 |
| hsa-miR-3163 | 2.41 | 4.0E−04 | 3.0E−02 | 4 | 10 |
| hsa-miR-155 | 2.44 | 1.8E−03 | 7.2E−02 | 397 | 968 |
| hsa-miR-371b-5p | 2.48 | 7.4E−03 | 1.3E−01 | 80 | 199 |
| hsa-miR-3128 | 3.00 | 1.0E−05 | 3.3E−03 | 34 | 102 |
| hsa-miR-4423-3p | 4.35 | 7.7E−06 | 3.2E−03 | 9 | 38 |
| hsa-miR-335 | 4.42 | 1.0E−06 | 2.3E−03 | 12 | 55 |
| hsa-miR-3201 | 4.91 | 4.4E−06 | 3.2E−03 | 51 | 248 |
| hsa-miR-184 | 7.73 | 8.0E−03 | 1.3E−01 | 2 | 19 |

TABLE 4

List of 40 modulated mature microRNAs (|fold| ≥1.5 and raw p-value ≤0.05) in the RII vs RI differential analysis (Blume rosacea study: GRDS0050) starting with 3391 Affymetrix identifiers

| Affymetrix id | Fold Change | Raw PValue | FDR_BH | Mean expression RI | Mean expression RII |
|---|---|---|---|---|---|
| hsa-miR-211 | −3.3 | 4.7E−03 | 3.9E−01 | 18 | 6 |
| hsa-miR-29b | −2.8 | 4.2E−02 | 6.4E−01 | 50 | 18 |
| hsa-miR-4324 | −2.6 | 4.6E−03 | 3.9E−01 | 15 | 6 |
| hsa-miR-143* | −2.5 | 5.0E−03 | 3.9E−01 | 19 | 8 |
| hsa-miR-1287 | −2.1 | 2.2E−02 | 5.8E−01 | 9 | 4 |
| hsa-miR-4708-5p | −2.0 | 1.3E−02 | 5.0E−01 | 23 | 11 |
| hsa-miR-195* | −2.0 | 1.0E−02 | 4.9E−01 | 11 | 6 |
| hsa-miR-508-5p | −1.9 | 1.2E−03 | 2.6E−01 | 11 | 6 |
| hsa-miR-204 | −1.9 | 1.2E−02 | 5.0E−01 | 7 | 4 |
| hsa-miR-96 | −1.9 | 1.0E−02 | 4.9E−01 | 6 | 3 |
| hsa-let-7b* | −1.8 | 4.4E−03 | 3.9E−01 | 11 | 6 |
| hsa-miR-935 | −1.8 | 6.2E−03 | 4.1E−01 | 7 | 4 |
| hsa-miR-675* | −1.7 | 1.3E−02 | 5.0E−01 | 6 | 4 |
| hsa-miR-149 | −1.7 | 5.3E−03 | 3.9E−01 | 663 | 396 |
| hsa-miR-30a* | −1.6 | 2.0E−04 | 1.2E−01 | 140 | 85 |
| hsa-miR-1181 | −1.6 | 1.6E−02 | 5.3E−01 | 11 | 7 |
| hsa-miR-506 | −1.6 | 4.9E−02 | 6.5E−01 | 5 | 3 |
| hsa-miR-23c | −1.6 | 1.6E−02 | 5.2E−01 | 70 | 45 |
| hsa-miR-127-5p | −1.5 | 7.7E−03 | 4.6E−01 | 4 | 3 |
| hsa-miR-491-5p | −1.5 | 1.3E−02 | 5.0E−01 | 37 | 24 |
| hsa-miR-4776-5p | 1.5 | 3.8E−03 | 3.9E−01 | 11 | 17 |
| hsa-miR-601 | 1.5 | 8.0E−04 | 2.1E−01 | 2 | 3 |
| hsa-miR-4530 | 1.5 | 2.2E−02 | 5.8E−01 | 906 | 1371 |
| hsa-miR-4773 | 1.5 | 2.2E−02 | 5.8E−01 | 8 | 12 |
| hsa-miR-4717-3p | 1.5 | 4.7E−03 | 3.9E−01 | 6 | 10 |
| hsa-miR-4657 | 1.6 | 1.4E−02 | 5.0E−01 | 9 | 14 |
| hsa-miR-4289 | 1.6 | 8.7E−03 | 4.6E−01 | 3 | 5 |
| hsa-miR-4417 | 1.6 | 9.1E−03 | 4.7E−01 | 34 | 56 |
| hsa-miR-4445* | 1.7 | 2.5E−02 | 6.1E−01 | 8 | 13 |
| hsa-miR-150 | 1.7 | 3.3E−02 | 6.1E−01 | 760 | 1258 |
| hsa-miR-146b-5p | 1.7 | 1.2E−02 | 5.0E−01 | 254 | 423 |
| hsa-miR-3175 | 1.8 | 1.2E−02 | 5.0E−01 | 14 | 25 |
| hsa-miR-4646-5p | 1.9 | 1.0E−03 | 2.3E−01 | 7 | 13 |
| hsa-miR-3163 | 1.9 | 5.3E−03 | 3.9E−01 | 6 | 10 |
| hsa-miR-4423-3p | 1.9 | 1.5E−02 | 5.2E−01 | 20 | 38 |
| hsa-miR-3128 | 2.2 | 4.0E−04 | 1.5E−01 | 47 | 102 |
| hsa-miR-1244 | 2.3 | 5.4E−02 | 3.9E−01 | 7 | 15 |
| hsa-miR-21* | 2.4 | 1.9E−02 | 5.8E−01 | 12 | 29 |
| hsa-miR-3201 | 2.4 | 1.8E−03 | 3.2E−01 | 102 | 248 |
| hsa-miR-335 | 3.9 | 2.5E−06 | 8.4E−03 | 14 | 55 | c) Filtering of Data on Expression Levels

Analysis of the experimental data was restricted to the microRNA expression values (mature and precursor), i.e., 3391 identifiers (probe sets) among the 5683 specific human identifiers. With the aim of eliminating the too-low expression levels and thus of limiting the background noise, the experimental data were filtered. Only genes having at least 5 of their expression values greater than the set threshold, i.e., at least 5/7 HV or 5/8 RI or 5/9 RII, were retained for the analysis. First, the dynamic range representing the number of identifiers as a function of expression level was produced, and a histogram was used to estimate the average threshold to exceed the background noise. Several filters were tested:

$Log_2$(Expression) greater than or equal to 1, i.e., Expression greater than or equal to 2, $Log_2$(Expression) greater than or equal to 1.5, i.e., Expression greater than or equal to 3, $Log_2$(Expression) greater than or equal to 2, i.e., Expression greater than or equal to 4, $Log_2$(Expression) greater than or equal to 2.5, i.e., Expression greater than or equal to 6, $Log_2$(Expression) greater than or equal to 3, i.e., Expression greater than or equal to 8.

To compare the results obtained by means of these various filters, differential analyses (RII individuals versus healthy individuals) were performed. These analyses made it possible to produce lists of significantly modulated microRNAs, i.e., respecting the selection criteria set forth below:

A false-positive rate less than or equal to 5% (FDR≤0.05) |fold|≥1.5

Table 5 below summarizes the results obtained.

TABLE 5

Results of the RII vs HV differential analysis after RMA normalization and expression level filtering

| Filter | Number of probe sets (IDs) | | RII vs HV differential analysis | | |
|---|---|---|---|---|---|
| | Before filtering on expression | After filtering on expression | Modulated microRNAs pre + mature) | Modulated mature microRNAs* | Modulated mature microRNAs** |
| No filter $Log_2$ (expression) | 3391 | 3391 (100%) | 39 (22+/17−) | 29 (12+/17−) | 160 |
| $Log_2$ (expression) ≥1 | 3391 | 2878 (85%) | 42 (23+/19−) | 33 (14+/1−) | 160 |
| $Log_2$ (expression) ≥1.5 | 3391 | 1355 (40%) | 81 (43+/38−) | 63 (28+/35−) | 160 |
| $Log_2$ (expression) ≥2 | 3391 | 937 (28%) | 102 (50+/52−) | 81 (32+/49−) | 160 |
| $Log_2$ (expression) ≥2.5 | 3391 | 757 (22%) | 98 (46+/52−) | 83 (33+/50−) | 160 |
| $Log_2$ (expression) ≥3 | 3391 | 648 (19%) | 100 (48+/52−) | 85 (35+/50−) | 160 |

*human microRNAs with |Fold| ≥ 1.5 and FDR ≤ 0.05
**human microRNAs with |Fold| ≥ 1.5 and p-value ≤ 0.05

It is important to note that the differences found by playing with the various filters relate only to FDR values. Indeed, neither the p-value nor the fold change are impacted. To illustrate the importance of the FDR, the list of significantly modulated mature microRNAs was established on the basis of a p-value≤0.05 and |Fold|≥1.5. By this method, 160 mature microRNAs are modulated; this corresponds to a false discovery rate of 50% when based on the list of 81 modulated mature microRNAs (FDR≤0.05 and |Fold|≤1.5) with the filter $log_2$(Expression)≥2. Only mature microRNAs were considered insofar as it is these which provide the biological function of regulating mRNAs. Furthermore, for these microRNAs, the signal corresponding to their respective precursors was too weak to pass the expression level filter.

The intersections between the lists of significantly modulated mature microRNAs were determined. Among the 81 mature microRNAs found to be significantly modulated with the filter $Log_2$(expression)≥2:

The 29 found to be significantly modulated were revealed without applying the expression level filter; there is thus no loss of information.

70 microRNAs are in common with the more stringent filter $Log_2$(expression)≥3; there is thus a gain of information by the addition of 41 microRNAs to the initial unfiltered list of 29.

Furthermore, if one is interested in microRNAs that diverge between the lists established with the filters $Log_2$(expression)≥2 and $Log_2$(expression) 3, one notices that:

8 microRNAs are included only in the list with the filter $Log_2$(expression) 2; their expression levels do not pass the filter $Log_2$(expression) 3, which means that information is lost, 15 microRNAs are included only in the list with the filter $Log_2$(expression) 3; their FDRs are between 0.05 and 0.06 when the filter $Log_2$(expression) 2 has been applied.

In conclusion, in this study, the filter $Log_2$(expression)≥2 was selected to eliminate a maximum of background noise, without however losing information, before performing the differential analyses.

d) List of Significantly Modulated microRNAs in RII Vs HV

Among the 81 significantly modulated microRNAs with FDR 0.05 and |fold|≥1.5, 32 are overexpressed and 49 are underexpressed in RII.

TABLE 6

List of underexpressed (left panel) and overexpressed (right panel) microRNAs in RII compared with healthy individuals

| probe set id | Fold | FDR | probe set id | Fold | FDR |
|---|---|---|---|---|---|
| hsa-miR-133a | −45.8 | 4.74E−02 | hsa-miR-3201 | 4.9 | 9.00E−04 |
| hsa-miR-133b | −39.0 | 3.08E−02 | hsa-miR-4423-3p | 4.4 | 9.00E−04 |
| hsa-miR-1 | −9.7 | 2.50E−02 | hsa-miR-3128 | 3.0 | 1.00E−03 |
| hsa-miR-299-5p | −5.1 | 3.09E−02 | hsa-miR-155 | 2.4 | 2.73E−02 |
| hsa-miR-486-3p | −4.7 | 4.24E−02 | hsa-miR-3163 | 2.4 | 1.02E−02 |
| hsa-miR-381 | −3.5 | 4.82E−02 | hsa-miR-146b-5p | 2.3 | 8.50E−03 |
| hsa-miR-4324 | −3.5 | 1.60E−02 | hsa-miR-606 | 2.2 | 3.61E−02 |
| hsa-miR-154 | −3.5 | 6.00E−04 | hsa-miR-150 | 2.1 | 3.56E−02 |
| hsa-miR-1247 | −3.4 | 8.90E−03 | hsa-miR-4776-5p | 2.1 | 9.00E−04 |
| hsa-miR-1287 | −3.3 | 1.74E−02 | hsa-miR-3124-5p | 1.9 | 2.76E−02 |
| hsa-miR-376c | −2.8 | 4.50E−02 | hsa-miR-4741 | 1.9 | 1.80E−02 |
| hsa-miR-195* | −2.8 | 1.28E−02 | hsa-miR-635 | 1.9 | 2.56E−02 |
| hsa-miR-4269 | −2.6 | 1.20E−03 | hsa-miR-4668-5p | 1.8 | 8.50E−03 |
| hsa-miR-1296 | −2.5 | 6.70E−03 | hsa-miR-4763-3p | 1.8 | 2.76E−02 |
| hsa-miR-34c-3p | −2.5 | 1.80E−03 | hsa-miR-4417 | 1.8 | 4.24E−02 |
| hsa-miR-204 | −2.5 | 2.13E−02 | hsa-miR-1911* | 1.8 | 4.55E−02 |
| hsa-miR-504 | −2.5 | 2.80E−02 | hsa-miR-4734 | 1.7 | 2.76E−02 |
| hsa-miR-30c-1* | −2.5 | 8.30E−03 | hsa-miR-4530 | 1.7 | 4.20E−02 |
| hsa-miR-615-3p | −2.4 | 2.70E−03 | hsa-miR-4260 | 1.7 | 3.86E−02 |
| hsa-miR-505 | −2.3 | 4.24E−03 | hsa-miR-3185 | 1.7 | 4.24E−02 |
| hsa-miR-508-5p | −2.3 | 5.90E−03 | hsa-miR- | 1.7 | 4.24E−02 |

TABLE 6-continued

List of underexpressed (left panel) and overexpressed
(right panel) microRNAs in RII compared with healthy individuals

| probe set id | Fold | FDR | probe set id | Fold | FDR |
|---|---|---|---|---|---|
| | | | 4707-5p | | |
| hsa-miR-409-5p | -2.3 | 4.36E-02 | hsa-miR-4745-5p | 1.7 | 3.50E-02 |
| hsa-miR-433 | -2.2 | 3.50E-02 | hsa-miR-4659a-3p | 1.7 | 1.28E-02 |
| hsa-miR-375 | -2.2 | 1.88E-02 | hsa-miR-1469 | 1.7 | 1.45E-02 |
| hsa-miR-935 | -2.2 | 1.72E-02 | hsa-miR-4695-5p | 1.7 | 1.88E-02 |
| hsa-miR-128 | -2.1 | 2.73E-02 | hsa-miR-4674 | 1.6 | 3.50E-02 |
| hsa-miR-331-5p | -2.1 | 4.44E-02 | hsa-miR-4687-3p | 1.6 | 6.60E-03 |
| hsa-miR-584 | -2.0 | 4.02E-02 | hsa-miR-4739 | 1.6 | 3.29E-02 |
| hsa-miR-30a* | -1.9 | 1.00E-03 | hsa-miR-1915 | 1.6 | 3.50E-02 |
| hsa-miR-370 | -1.9 | 6.50E-03 | hsa-miR-216b | 1.6 | 4.15E-02 |
| hsa-miR-148a* | -1.9 | 3.68E-02 | hsa-miR-548a-3p | 1.5 | 4.00E-02 |
| hsa-miR-489 | -1.9 | 4.24E-02 | | | |
| hsa-miR-30e* | -1.8 | 4.24E-02 | | | |
| hsa-miR-337-5p | -1.8 | 3.01E-02 | | | |
| hsa-miR-1181 | -1.8 | 4.55E-02 | | | |
| hsa-miR-1237 | -1.8 | 3.61E-02 | | | |
| hsa-miR-485-5p | -1.7 | 2.76E-02 | | | |
| hsa-miR-23c | -1.7 | 4.20E-02 | | | |
| hsa-miR-148b | -1.7 | 1.66E-02 | | | |
| hsa-miR-378g | -1.7 | 2.26E-02 | | | |
| hsa-miR-1238 | -1.7 | 4.55E-02 | | | |
| hsa-miR-181a-2* | -1.6 | 3.50E-02 | | | |
| hsa-miR-187 | -1.6 | 4.20E-02 | | | |
| hsa-miR-378d | -1.6 | 1.51E-02 | | | |
| hsa-miR-181d | -1.6 | 2.69E-02 | | | |
| hsa-miR-98 | -1.5 | 4.24E-02 | | | |
| hsa-miR-4685-3p | -1.5 | 4.24E-02 | | | |
| hsa-miR-23b* | -1.5 | 4.24E-02 | | | | e) Hierarchical Clustering

With the aim of confirming that the 81 mature microRNAs expressed differentially in RII according to Affymetrix technology can be used to differentiate affected individuals from healthy individuals, hierarchical clustering was performed in Array Studio (results not shown).

Two characteristic groups are revealed:
A group consisting of 6 healthy subjects
A group consisting of 9 subjects with subtype II rosacea and 1 healthy subject.

This healthy subject shows an atypical expression profile, similar neither to RII subjects nor to HV subjects. Furthermore, in a previous study, this individual was also classified in a group of affected subjects when mRNA clustering was performed. In conclusion, despite one conflicting individual, the microRNA expression profiles make it possible to differentiate affected individuals from healthy individuals.

MicroRNA Biomarker(s)

In order to reveal potential microRNA biomarkers of PPR rosacea, the intersection of the lists of significantly modulated microRNAs in three studies characterizing the miR-Nome in skin pathologies was determined. These studies concern:

the present project: characterization of the miRNome in rosacea (RII versus HV).

another study: characterization of the miRNome in acneic lesional skin (study carried out under the same experimental conditions as the rosacea study) versus non-lesional skin.

an external study: characterization of the miRNome in psoriasis (Zibert et al. J Dermatol Sci. 2010 58(3): 177-85) carried out with technologies different from those used herein (smaller panel of microRNAs studied).

The results of these intersections showed a significant proportion of microRNAs specifically expressed for each of these pathologies.

Thus, 76 microRNAs are specifically expressed in type II rosacea. Among these 76 microRNAs, 27 are overexpressed in RII (compared with HV). A biomarker should preferably be strongly expressed in the pathology and weakly or not expressed in healthy individuals. Based on both fold change (the highest possible) and expression in healthy skin (the lowest possible), a list of 7 potential biomarkers of type II rosacea was established. This list comprises the microRNAs hsa-miR-606, hsa-miR-635, hsa-miR-3128, hsa-miR-3163, hsa-miR-3201, hsa-miR-4423-3p and hsa-miR-4776-5p (shown in the box below).

TABLE 7

List of 27 microRNAs overexpressed in RII (not modulated in the acne and psoriasis studies)

| miRBase (mature) | RII vs HV Fold change | Mean expression HV (rosacea study) | Mean expression RII | RII vs RI Fold change | Mean expression RI | Acne vs HV Fold change | Mean expression HV (acne study) |
|---|---|---|---|---|---|---|---|
| hsa-miR-3201 | 4.9 | 51 | 248 | 2.4 | 102* | -1.1 | 46 |
| hsa-miR-4423-3p | 4.4 | 9 | 38 | 1.9 | 20* | -1.3 | 10 |
| hsa-miR-3128 | 3.0 | 34 | 102 | 2.2 | 47 | -1.1 | 18 |
| hsa-miR-3163 | 2.4 | 4 | 10 | 1.9 | 6 | -1.2 | 5 |
| hsa-miR-606 | 2.2 | 3 | 7 | 1.6 | 5 | does not pass the expression filter | |
| hsa-miR-4776-5p | 2.1 | 8 | 17 | 1.5 | 11 | -1.2 | 5 |
| hsa-miR-635 | 1.9 | 8 | 14 | 1.3 | 11 | 1.1 | 5 |
| hsa-miR-3124-5p | 1.9 | 46 | 88 | 1.3 | 69 | -1.2 | 26 |
| hsa-miR-4741 | 1.9 | 288 | 537 | 1.2 | 439* | -1.4 | 397 |
| hsa-miR-4668-5p | 1.8 | 1388 | 2476 | 1.2 | 2027 | -1.3 | 1489 |
| hsa-miR-4763-3p | 1.8 | 1235 | 2182 | 1.2 | 1889* | -1.3 | 1756 |
| hsa-miR-1911* | 1.8 | 3 | 5 | 1.1 | 4* | does not pass the expression filter | |
| hsa-miR-4734 | 1.7 | 855 | 1495 | 1.1 | 26* | -1.4 | 1196 |
| hsa-miR-4530 | 1.7 | 786 | 1371 | 1.5 | 906 | -1.3 | 1091 |
| hsa-miR-4260 | 1.7 | 3 | 6 | 1.4 | 4 | does not pass the expression filter | |

TABLE 7-continued

List of 27 microRNAs overexpressed in RII (not modulated in the acne and psoriasis studies)

| miRBase (mature) | RII vs HV Fold change | Mean expression HV (rosacea study) | Mean expression RII | RII vs RI Fold change | Mean expression RI | Acne vs HV Fold change | Mean expression HV (acne study) |
|---|---|---|---|---|---|---|---|
| hsa-miR-3185 | 1.7 | 479 | 816 | 1.1 | 743* | −1.3 | 628 |
| hsa-miR-4707-5p | 1.7 | 903 | 1535 | 1.1 | 1353* | −1.3 | 1200 |
| hsa-miR-4745-5p | 1.7 | 1374 | 2321 | 1.2 | 1956 | −1.3 | 1518 |
| hsa-miR-4659a-3p | 1.7 | 2 | 4 | 1.5 | 3 | does not pass the expression filter | |
| hsa-miR-1469 | 1.7 | 2171 | 3606 | 1.2 | 3000 | −1.2 | 2692 |
| hsa-miR-4695-5p | 1.7 | 325 | 537 | 1.3 | 416 | −1.2 | 299 |
| hsa-miR-4674 | 1.6 | 388 | 640 | 1.2 | 549 | −1.4 | 470 |
| hsa-miR-4687-3p | 1.6 | 2168 | 3569 | 1.3 | 2748 | −1.2 | 2724 |
| hsa-miR-4739 | 1.6 | 753 | 1221 | 1.2 | 1005 | −1.1 | 929 |
| hsa-miR-1915 | 1.6 | 3941 | 6301 | 1.2 | 5260 | −1.3 | 5594 |
| hsa-miR-216b | 1.6 | 3 | 5 | 1.3 | 4 | does not pass the expression filter | |
| hsa-miR-548a-3p | 1.5 | 23 | 35 | 1.1 | 32 | −1.1 | 19 |

*| Fold change Mean expression | ≥1.5 in RI vs HV

Materials and Methods
Total RNA Extraction (mRNA and microRNAs)

Total RNA extraction was performed beforehand in order to carry out a transcriptome study. This extraction was performed with the miRNeasy Mini Kit from QIAGEN which extracts large RNAs (mRNA) as well as small RNAs including microRNAs. This kit comprises three successive steps: lysing tissues to release RNAs contained in cells, isolating RNAs on a membrane, then eluting them. The results of the transcriptome study previously established were used for the biological interpretation of the data on the microRNAs obtained.

Large-Scale Study of microRNAs

Study of microRNA Gene Expression: Affymetrix miRNA Chip

The miRNA 3.0 chip consists of nucleic acid fragments, called probes, bound to a physical substrate and whose sequence set corresponds to the microRNAs of 153 organisms including more than 1700 mature forms of human microRNAs. Each probe (single-stranded DNA fragment) is complementary to a given microRNA. For each microRNA, several probes, sometimes varying by a few base pairs, are present on the chip. This is called a probe set. The miRNA 3.0 chip contains nearly 20,000 probe sets of which more than 5600 are specific to small human RNAs, including microRNAs (1733 matures and 1658 precursors). The design of this chip was based on miRBase version 17. A probe set dedicated to a mature microRNA is composed of 9 identical probes, complementary to the sequence of the target mature RNA.

The experiment is carried out starting with 300 ng of total RNA. The first step consists in adding a poly(A) tail to the microRNAs. This poly(A) tail, initially present on the mRNAs and thereafter also on the microRNAs, will allow the binding of the 3DNA® molecule labeled with 15 biotins. The result is the formation of biotinylated RNAs. The second phase is hybridization of the RNAs to their respective probes; as the probes present in the various compartments of the chip are specific to microRNAs, biotinylated mRNAs are excluded while biotinylated microRNAs hybridize to the probes. Washing eliminates the molecules not hybridized to the chip. In a third step, streptavidin coupled to a fluorescent molecule, phycoerythrin, is added. Thanks to its affinity for biotin, streptavidin makes it possible to detect biotinylated microRNAs. To optimize this labeling, an amplification of the labeling is performed: to this end, a goat anti-streptavidin antibody coupled to biotin is introduced. This last will bind to the preceding biotinylated microRNA-streptavidin/phycoerythrin complex. A second addition of streptavidin/phycoerythrin will have the effect of amplifying the fluorescent label to improve detection. The successive labeling and washing steps are automated thanks to a dedicated Affymetrix platform. The fluorescent signal is then processed by means of the Expression Console Software, provided by Affymetrix. The greater the quantity of microRNA bound to its complementary probe, the stronger the light signal. Thus, for each chip, it is by comparing the light intensity corresponding to each probe of a treated sample versus a control sample that the effect of this treatment on gene expression can be analyzed.

Biostatistics

From a technical perspective, transcriptome studies are both reliable and affordable. However, analysis of the large amounts of data generated remains a crucial point. In this area, resorting to bioinformatic tools and biostatistics is essential. There remains no consensus concerning the choice of mathematical algorithms used to treat these data. For miRNome studies in particular, whether on a large scale or a smaller scale by qPCR, several methods for normalizing raw data have been proposed. Concerning large-scale studies of microRNA expression, the most commonly used method today is RMA normalization. Before normalization, the expression data are transformed to $\log_2$ to produce a linear range and to reduce the extent of the data.

Array Studio software: Array Studio is a software package designed for biologists and bioinformatics scientists to statistically analyze new-generation sequencing data, SNPs or microarrays. It includes in particular support for all microarray platforms, including Agilent, Illumina and Affymetrix, the latter being used in the context of our study. First, it makes it possible to normalize raw data by various methods and, second, to carry out intergroup differential analyses to compare microRNA expression profiles.

Robust Multiarray/Multichip Average (RMA) normalization: Large-scale studies now make it possible to analyze the expression profiles of numerous genes in a single experiment; for example, to characterize an individual's miR-Nome. These experiments, repeated for each sample (individual) tested, generate a great deal of data but these data may be biased by technological variations. The goal of normalization is to remove technology-related noise in order to take biological variations into account as precisely as possible. RMA normalization comprises three successive steps: background noise correction; quantile normalization: carried out on all the chips of the study concerned and tends to homogenize expression level distributions between chips in order to analyze them jointly or to compare them; and "median polish": the step during which the fluorescence intensities of targets binding to the same probe set are combined in order to estimate a single intensity value, per chip, for each target set (or gene).

Differential Analyses

Once the expression levels are normalized, intergroup differential analyses make it possible to compare:
  individuals from the rosacea I subgroup with the subgroup of healthy individuals,
  individuals from the rosacea II subgroup with the subgroup of healthy individuals,
  individuals from the rosacea II subgroup with those from the rosacea I subgroup.

Thus, the characterization of the miRNome in a pathological condition is achieved by comparison with the microRNA profiles obtained in a healthy condition. The principle of this comparison rests on the calculation of fold change (change in gene expression level). To know the confidence level given to this fold, a p-value is associated therewith, calculated using a hypothesis test called Student's t-test.

Calculation of Fold Change a) Relative Expression of Large-Scale Data (Affymetrix)

Since the normalized expression data were transformed to $\log_2$, relative expression is calculated as follows:

Relative expression=$2^\Delta$ with $\Delta = \log_2(\text{Mean expression}_{gene/condition\ B}) - \log_2(\text{Mean expression}_{gene/condition\ A/reference})$ b) Fold Change Fold change is expressed as the change in the mean expression of gene i in condition A (reference) relative to condition B; if the fold change is positive then gene i is overexpressed in condition A relative to control condition B. Conversely, if the fold change is negative then gene i is underexpressed in condition A relative to control condition B. If the calculated relative expression value is greater than 1, it is equivalent to a positive fold change. On the other hand, if the calculated relative expression is between 0 and 1, meaning that the gene is expressed more in the reference condition (A) than in the test condition (B), the operation −1/fold is then carried out to obtain negative fold change values, which are more easily interpretable. A fold threshold may be set by the biologist to specifically select those having biological interest; in this study, it is set at +/−1.5.

Principle of a Hypothesis Test

In statistics, a hypothesis test consists in evaluating a statistical hypothesis with respect to a data set (sample). For example, if one asks the question: Is gene i differentially expressed in condition A relative to condition B? Condition A may correspond to affected individuals and condition B to healthy control individuals.

To answer yes or no to the question involves deciding between two hypotheses:
  The null hypothesis (H0): the gene is not differentially expressed,
  The alternative hypothesis (H1): the gene is differentially expressed.

Two types of errors may arise:
  A type I error: rejecting H0 when H0 is true, amounts to considering that the gene is differentially expressed when it is not; this is a false-positive.
  A type II error: not rejecting H0 when H0 is false, amounts to considering that the gene is not differentially expressed when it actually is; this is a false-negative.

The maximum tolerated risk (denoted a) is called the significance threshold; it is generally set at 0.05. In our example, that amounts on average to accepting the risk of being mistaken 5 times out of 100 and thus accepting on average 5% false-positives in our analysis.

The test statistic is calculated from the data. Its value makes it possible to estimate the probability (p-value) necessary to obtain these data if H0 is true. As a function of the significance threshold set beforehand and this p-value, the decision to reject or not to reject H0 may be made.

Student's Test or t-Test

This test makes it possible to evaluate whether the expression means of gene i in each condition A and B are statistically different from each other and thus to compare one condition relative to another. The p-value of the t-test then makes it possible to conclude whether the difference between the averages is not due to chance:
  If the p-value 0.05 then H0 is rejected; the averages of the two conditions A and B are said to be significantly different, gene i is thus modulated significantly in condition A relative to condition B.
  If the p-value>0.05 then H0 is not rejected; the averages of the two conditions A and B are said to be not significantly different, gene i is thus not modulated significantly in condition A relative to condition B.

Control of False Discovery Rate (FDR)

Expression chips for large-scale analyses make it possible to simultaneously measure the transcriptional activity of several thousand genes for a given biological sample. To analyze them simultaneously, the hypothesis tests are multiplied. However, when the tests are multiplied, the probability of detecting a significantly modulated gene, when it is not, increases. To control the false discovery rate (genes considered modulated when they are not), the false discovery rate is controlled using a method developed by Benjamini and Hochberg 1995, Journal of the Royal Statistical Society. Series B (Methodological) vol. 57, No. 1 (1995), pp. 289-300—the false discovery rate (FDR)—which corrects p-values associated with t-tests in order to select the same false discovery rate irrespective of the number of genes. In conclusion, after a differential analysis, gene i is considered significantly modulated if it meets two conditions:
  |fold|≥1.5
  FDR<0.05

The invention claimed is:

1. A method of detecting one or more biomarkers for rosacea in a subject, the method comprising:
  (a) obtaining a sample from said subject;
  (b) extracting RNA from the sample; and
  (c) detecting whether the one or more biomarkers for rosacea are present in the sample by contacting the RNA of step (b) with one or more nucleic acid probes for the following seven microRNAs: hsa-miR-3201, hsa-miR-4423-3p, hsa-miR-3128, hsa-miR-3163, hsamiR-606, hsa-miR-4776-5p and hsa-miR-635 and detecting binding between the RNA and the nucleic acid probe.

2. The method according to claim 1, further comprising additionally determining the expression of one or more microRNAs selected from the group consisting of:

| | |
|---|---|
| hsa-miR-133a | hsa-miR-3201 |
| hsa-miR-133b | hsa-miR-4423-3p |
| hsa-miR-1 | hsa-miR-3128 |
| hsa-miR-299-5p | hsa-miR-155 |
| hsa-miR-486-3p | hsa-miR-3163 |
| hsa-miR-381 | hsa-miR-146b-5p |
| hsa-miR-4324 | hsa-miR-606 |
| hsa-miR-154 | hsa-miR-150 |
| hsa-miR-1247 | hsa-miR-4776-5p |
| hsa-miR-1287 | hsa-miR-3124-5p |
| hsa-miR-376c | hsa-miR-4741 |
| hsa-miR-195* | hsa-miR-635 |
| hsa-miR-4269 | hsa-miR-4668-5p |
| hsa-miR-1296 | hsa-miR-4763-3p |
| hsa-miR-34c-3p | hsa-miR-4417 |
| hsa-miR-204 | hsa-miR-1911* |
| hsa-miR-504 | hsa-miR-4734 |
| hsa-miR-30c-1* | hsa-miR-4530 |
| hsa-miR-615-3p | hsa-miR-4260 |
| hsa-miR-505 | hsa-miR-3185 |
| hsa-miR-508-5p | hsa-miR-4707-5p |
| hsa-miR-409-5p | hsa-miR-4745-5p |
| hsa-miR-433 | hsa-miR-4659a-3p |
| hsa-miR-375 | hsa-miR-1469 |
| hsa-miR-935 | hsa-miR-4695-5p |
| hsa-miR-128 | hsa-miR-4674 |
| hsa-miR-331-5p | hsa-miR-4687-3p |
| hsa-miR-584 | hsa-miR-4739 |
| hsa-miR-30a* | hsa-miR-1915 |
| hsa-miR-370 | hsa-miR-216b and |
| hsa-miR-148a* | hsa-miR-548a-3p |
| hsa-miR-489 | |
| hsa-miR-30e* | |
| hsa-miR-337-5p | |
| hsa-miR-1181 | |
| hsa-miR-1237 | |
| hsa-miR-485-5p | |
| hsa-miR-23c | |
| hsa-miR-148b | |
| hsa-miR-378g | |
| hsa-miR-1238 | |
| hsa-miR-181a-2* | |
| hsa-miR-187 | |
| hsa-miR-378d | |
| hsa-miR-181d | |
| hsa-miR-98 | |
| hsa-miR-4685-3p | |
| hsa-miR-23b* | |

3. The method according to claim 1, further comprising additionally determining the expression of one or more microRNAs selected from one of the groups:
  a) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-4269, hsa-miR-1296, hsa-miR-34c-3p, hsa-miR-204, hsa-miR-504, hsa-miR-30c-1*, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-148b, hsa-miR-378g, hsa-miR-1238, hsa-miR-181a-2*, hsa-miR-187, hsa-miR-378d, hsa-miR-181d, hsa-miR-98, hsa-miR-4685-3p, hsa-miR-23b*, hsa-miR-3201, hsa-miR-4423-3p, hsa-miR-3128, hsa-miR-155, hsa-miR-3163, hsa-miR-146b-5p, hsa-miR-606, hsa-miR-150, hsa-miR-4776-5p, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, and hsa-miR-548a-3p;
  b) hsa-miR-223, hsa-miR-142-3p, hsa-miR-146b, hsa-miR-21, hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-125a-5p, mmu-miR-491, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, and hsa-miR-133a;
  c) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-885-5p, hsa-miR-1287, hsa-miR-95, hsa-miR-376c, hsa-miR-195*, hsa-miR-4269, mmu-miR-499, hsa-miR-1296, hsa-miR-34c-3p, hsa-miR-204, hsa-miR-504, hsa-miR-30c-1*, hsa-miR-487b, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-491-5p, hsa-miR-148b, hsa-miR-378g, hsa-miR-125a-5p, hsa-miR-1238, hsa-miR-181a-2*, hsa-miR-187, hsa-miR-30c, hsa-miR-27a, hsa-miR-99a, hsa-miR-378d, hsa-miR-181d, hsa-miR-98, hsa-miR-4685-3p, hsa-miR-598, hsa-miR-23b*, hsa-miR-3201, hsa-miR-4423-3p, hsa-miR-223, hsa-miR-3128, hsa-miR-155, hsa-miR-3163, hsa-miR-146b-5p, hsa-miR-606, hsa-miR-150, hsa-miR-4776-5p, hsa-miR-142-3p, hsa-miR-21, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, and hsa-miR-548a-3p; and
  d) hsa-miR-3201, hsa-miR-4423-3p, hsa-miR-3128, hsa-miR-3163, hsa-miR-606, hsa-miR-4776-5p, hsa-miR-635, hsa-miR-3124-5p, hsa-miR-4741, hsa-miR-4668-5p, hsa-miR-4763-3p, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, and hsa-miR-548a-3p.

4. The method according to claim 1, the method further comprising:
  (d) determining the level of expression of one or more microRNAs selected from the group consisting of hsa-miR-133a, hsa-miR-133b, hsa-miR-1, hsa-miR-486-3p, hsa-miR-34c-3p, hsa-miR-375 and hsa-miR-146b-5p.

5. The method according to claim 1, the method further comprising additionally determining the expression of one or more microRNAs selected from one of the groups consisting of:
  1) hsa-miR-4758-5p, hsa-miR-4665-5p, hsa-miR-149*, hsa-miR-548ac, hsa-miR-4507, hsa-miR-548a-3p, hsamiR-4289, hsa-miR-4727-3p, hsa-miR-4468, hsa-miR-4463, hsa-miR-2861, hsa-miR-4773, hsa-miR-1825, hsa-miR-4651, hsa-miR-216b, hsa-miR-4689, hsa-miR-3152-3p, hsa-miR-4270, hsa-miR-1915, hsa-miR-4739, hsa-miR-4772-5p, hsa-miR-4687-3p, hsa-miR-4674, hsa-miR-4695-5p, hsa-miR-4439, hsa-miR-129-3p, hsa-miR-1469, hsa-miR-4659a-3p, hsa-miR-4799-3p, hsa-miR-4657, hsa-miR-4655-5p, hsa-miR-4745-5p, hsa-miR-4662b, hsa-miR-4707-5p, hsa-miR-3185, hsa-miR-4260, hsa-miR-4530, hsa-miR-4734, hsa-miR-1911*, hsa-miR-4417, hsa-miR-4763-3p, hsa-miR-4668-5p, hsa-miR-1281, hsa-miR-635, hsa-miR-4741, hsa-miR-3124-5p, hsa-miR-146b-3p, hsa-miR-4529-3p, hsa-miR-4776-5p, hsa-miR-150, hsa-miR-3927, hsa-miR-606, hsa-miR-146b-5p, hsa-miR-3163, hsa-miR-155, hsa-miR-371b-5p, hsa-miR-3128, hsa-miR-4423-3p, hsa-miR-335, hsa-miR-3201, and hsa-miR-184;

2) hsa-miR-1269b, hsa-miR-4741, hsa-miR-4763-3p, hsa-miR-4704-5p, hsa-miR-1911*, hsa-miR-3621, hsa-miR-3612, hsa-miR-4436b-5p, hsa-miR-4734, hsa-miR-3185, hsa-miR-3910, hsa-miR-4727-3p, hsa-miR-155, hsa-miR-155*, hsa-miR-4529-3p, hsa-miR-3927, hsa-miR-3201, hsa-miR-4423-3p, hsa-miR-124, and hsa-miR-184;

3) hsa-miR-4776-5p, hsa-miR-601, hsa-miR-4530, hsa-miR-4773, hsa-miR-4717-3p, hsa-miR-4657, hsa-miR-4289, hsa-miR-4417, hsa-miR-4445*, hsa-miR-150, hsa-miR-146b-5p, hsa-miR-3175, hsa-miR-4646-5p, hsa-miR-3163, hsa-miR-4423-3p, hsa-miR-3128, hsa-miR-1244, hsa-miR-21*, hsa-miR-3201, and hsa-miR-335; and 4) hsa-miR-223, hsa-miR-142-3p, hsa-miR-146b, hsa-miR-21, hsa-miR-155;
    a) hsa-miR-3201, hsa-miR-4423-3p, hsa-miR-3128, hsa-miR-155, hsa-miR-3163, hsa-miR-146b-5p, hsa-miR-606, hsa-miR-150, hsa-miR-4776-5p, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p;
    b) hsa-miR-223, hsa-miR-142-3p, hsa-miR-146b, hsa-miR-21;
    c) hsa-miR-3201, hsa-miR-4423-3p, hsa-miR-223, hsa-miR-3128, hsa-miR-155, hsa-miR-3163, hsa-miR-146b-5p, hsa-miR-606, hsa-miR-150, hsa-miR-4776-5p, hsa-miR-142-3p, hsa-miR-21, hsa-miR-3124-5p, hsa-miR-4741, hsa-miR-635, hsa-miR-4668-5p, hsa-miR-4763-3p, hsa-miR-4417, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p;
    d) hsa-miR-3201, hsa-miR-4423-3p, hsa-miR-3128, hsa-miR-3163, hsa-miR-606, hsa-miR-4776-5p, hsa-miR-635, hsa-miR-3124-5p, hsa-miR-4741, hsa-miR-4668-5p, hsa-miR-4763-3p, hsa-miR-1911*, hsa-miR-4734, hsa-miR-4530, hsa-miR-4260, hsa-miR-3185, hsa-miR-4707-5p, hsa-miR-4745-5p, hsa-miR-4659a-3p, hsa-miR-1469, hsa-miR-4695-5p, hsa-miR-4674, hsa-miR-4687-3p, hsa-miR-4739, hsa-miR-1915, hsa-miR-216b, hsa-miR-548a-3p; and
    e) hsa-miR-146b-5p.

6. The method according to claim 1, further comprising additionally determining in a sample from said subject the expression of one or more microRNAs selected from the group consisting of:

1) hsa-miR-133a, hsa-miR-206, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-411, hsa-miR-4269, hsa-miR-328, hsa-miR-1296, hsa-miR-34c-3p, hsa-miR-204, hsa-miR-504, hsa-miR-30c-1*, hsa-miR-615-3p, hsa-miR-654-3p, hsa-miR-505, hsa-miR-508-5p, hsa-miR-409-5p, hsa-miR-338-5p, hsa-miR-433, hsa-miR-375, hsa-miR-935, hsa-let-7d*, hsa-miR-99a*, hsa-miR-128, hsa-miR-1290, hsa-miR-331-5p, hsa-miR-4730, hsa-miR-29c*, hsa-miR-455-5p, hsa-miR-377*, hsa-miR-378e, hsa-miR-584, hsa-miR-96, hsa-miR-30a*, hsa-miR-143*, hsa-miR-370, hsa-miR-148a*, hsa-miR-489, hsa-miR-506, hsa-let-7e*, hsa-miR-30e*, hsa-miR-4787-3p, hsa-let-7b*, hsa-miR-181c*, hsa-miR-513a-5p, hsa-miR-92a-1*, hsa-miR-337-5p, hsa-miR-1181, hsa-miR-1237, hsa-miR-3620, hsa-miR-485-5p, hsa-miR-23c, hsa-miR-18a*, hsa-miR-10a, hsa-miR-139-3p, hsa-miR-493, hsa-miR-148b, hsa-miR-550a, hsa-miR-3147, hsa-miR-378g, hsa-miR-675*, hsa-miR-1238, hsa-miR-542-5p, hsa-miR-30c-2*, hsa-miR-125a-3p, hsa-miR-181a-2*, hsa-miR-1292, hsa-miR-187, hsa-miR-378*, hsa-miR-493*, hsa-miR-495, hsa-miR-557, hsa-miR-3909, hsa-miR-378d, hsa-miR-491-5p, hsa-miR-181d, hsa-miR-671-3p, hsa-miR-513c, hsa-miR-487b, hsa-miR-378b, hsa-miR-885-5p, hsa-miR-98, hsa-miR-29b-2*, hsa-miR-4685-3p, hsa-miR-3605-3p, hsa-miR-24-1*, hsa-miR-4649-3p, hsa-miR-3180-5p, hsa-miR-149, hsa-miR-23b*;

2) hsa-miR-206, hsa-miR-133b, hsa-miR-133a, hsa-miR-1, hsa-miR-486-3p, hsa-miR-299-5p, hsa-miR-1247, hsa-miR-381, hsa-miR-154, hsa-miR-433, hsa-miR-1244, hsa-miR-4485, hsa-miR-378e, hsa-miR-505, hsa-miR-376c, hsa-miR-1296, hsa-miR-29b-1*, hsa-miR-409-5p, hsa-miR-29c*, hsa-miR-34c-3p, hsa-miR-4646-5p, hsa-miR-99a*, hsa-miR-378g, hsa-miR-504, hsa-miR-584, hsa-miR-128, hsa-miR-30c-1*, hsa-miR-665, hsa-miR-4269, hsa-miR-493*, hsa-miR-328, hsa-miR-550a, hsa-miR-375, hsa-miR-493, hsa-miR-378d, hsa-miR-148a*, hsa-miR-615-3p, hsa-miR-431*, hsa-miR-378i, hsa-miR-422a, hsa-miR-331-5p, hsa-miR-378*, hsa-miR-148b, hsa-miR-601, hsa-miR-4288, hsa-miR-596, hsa-miR-10a, hsa-miR-200c*, hsa-miR-378b, hsa-miR-378f, hsa-miR-4257, hsa-miR-370, hsa-miR-1237, hsa-miR-3942-3p;

3) hsa-miR-211, hsa-miR-29b, hsa-miR-4324, hsa-miR-143*, hsa-miR-1287, hsa-miR-4708-5p, hsa-miR-195*, hsa-miR-508-5p, hsa-miR-204, hsa-miR-96, hsa-let-7b*, hsa-miR-935, hsa-miR-675*, hsa-miR-149, hsa-miR-30a*, hsa-miR-1181, hsa-miR-506, hsa-miR-23c, hsa-miR-127-5p, hsa-miR-491-5p; and 4) hsa-miR-30b, hsa-miR-221, hsa-miR-141, hsa-miR-339-3p, hsa-miR-100, hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-199a, hsa-miR-125a-5p, mmu-miR-491, hsa-miR-489, hsa-miR-337-5p, hsa-miR-149, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a;

a) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-1287, hsa-miR-376c, hsa-miR-195*, hsa-miR-4269, hsa-miR-1296, hsa-miR-34c-3p, hsa-miR-204, hsa-miR-504, hsa-miR-30c-1*, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-148b, hsa-miR-378g, hsa-miR-1238, hsa-miR-181a-2*, hsa-miR-187, hsa-miR-378d, hsa-miR-181d, hsa-miR-98, hsa-miR-4685-3p, hsa-miR-23b*;

b) hsa-miR-331, hsa-miR-598, hsa-miR-24, hsa-miR-23a, hsa-miR-99a, hsa-miR-152, hsa-miR-423-5p, hsa-miR-34c, hsa-miR-27a, hsa-miR-30c, hsa-miR-125a-5p, mmu-miR-491, hsa-miR-127, hsa-miR-375, hsa-miR-101, hsa-miR-296, mmu-miR-379, hsa-miR-574-3p, hsa-miR-487b, mmu-miR-499, hsa-miR-95, hsa-miR-885-5p, hsa-miR-486-3p, hsa-miR-1, hsa-miR-133b, hsa-miR-133a;

c) hsa-miR-133a, hsa-miR-133b, hsa-miR-1, hsa-miR-299-5p, hsa-miR-486-3p, hsa-miR-381, hsa-miR-4324, hsa-miR-154, hsa-miR-1247, hsa-miR-885-5p, hsa-miR-1287, hsa-miR-95, hsa-miR-376c, hsa-miR-195*, hsa-miR-4269, mmu-miR-499, hsa-miR-1296, hsa-miR-34c-3p, hsa-miR-204, hsa-miR-504, hsa-miR-30c-1*, hsa-miR-487b, hsa-miR-615-3p, hsa-miR-505, hsa-miR-508-5p, hsa-miR-409-5p, hsa-miR-433, hsa-miR-375, hsa-miR-935, hsa-miR-128, hsa-miR-331-5p, hsa-miR-584, hsa-miR-30a*, hsa-miR-370, hsa-miR-148a*, hsa-miR-489, hsa-miR-30e*, hsa-miR-337-5p, hsa-miR-1181, hsa-miR-1237, hsa-miR-485-5p, hsa-miR-23c, hsa-miR-491-5p, hsa-miR-148b, hsa-miR-378g, hsa-miR-125a-5p, hsa-miR-1238, hsa-miR-181a-2*, hsa-miR-187, hsa-miR-30c, hsa-miR-27a, hsa-miR-99a, hsa-miR-378d, hsa-miR-181d, hsa-miR-98, hsa-miR-4685-3p, hsa-miR-598, hsa-miR-23b*; and d) hsa-miR-133a, hsa-miR-133b, hsa-miR-1, hsa-miR-486-3p, hsa-miR-34c-3p, hsa-miR-375.

7. The method according to claim 1, wherein the rosacea is a type II rosacea.

\* \* \* \* \*